US009321128B2

(12) United States Patent
Bradley et al.

(10) Patent No.: US 9,321,128 B2
(45) Date of Patent: Apr. 26, 2016

(54) HIGH POWER LASER SYSTEM

(71) Applicants: Timothy Bradley, Loogootee, IN (US); Eric Hillenbrand, Evansville, IN (US)

(72) Inventors: Timothy Bradley, Loogootee, IN (US); Eric Hillenbrand, Evansville, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 175 days.

(21) Appl. No.: 13/734,397

(22) Filed: Jan. 4, 2013

(65) Prior Publication Data

US 2013/0140283 A1 Jun. 6, 2013

Related U.S. Application Data

(60) Division of application No. 12/778,643, filed on May 12, 2010, now Pat. No. 8,420,977, which is a continuation-in-part of application No. 12/511,056, filed on Jul. 28, 2009, now Pat. No. 8,436,276.

(51) Int. Cl.
*F41H 13/00* (2006.01)
*B23K 26/00* (2014.01)
(Continued)

(52) U.S. Cl.
CPC ......... *B23K 26/0096* (2013.01); *A61K 31/7105* (2013.01); *C12Q 1/6886* (2013.01); *C12Q 1/708* (2013.01); *F41H 13/0056* (2013.01); *C12Q 2600/112* (2013.01); *C12Q 2600/158* (2013.01)

(58) Field of Classification Search
CPC ..... F41H 13/0056; F41H 13/00; F41H 11/02; F41H 13/005; F41H 13/0062; G01S 7/495; G01S 13/865; G01S 17/023; G01S 7/36

USPC ................................ 356/5.01; 244/3.16, 3.17
See application file for complete search history.

(56) References Cited

U.S. PATENT DOCUMENTS 3,392,259 A 7/1968 Meier
3,622,743 A 11/1971 Muncheryan
(Continued)

FOREIGN PATENT DOCUMENTS

WO    WO 99/07439    2/1999
WO    WO 2006/031351    3/2006

OTHER PUBLICATIONS

Wagner et al, Infrared semiconductor lasers for DIRCM applications, Proc. SPIE 7115, Technologies for Optical Countermeasures V, 71150A (Oct. 2, 2008).*

(Continued)

*Primary Examiner* — Luke Ratcliffe
*Assistant Examiner* — Vicente Rodriguez
(74) *Attorney, Agent, or Firm* — Christopher A. Monsey

(57) ABSTRACT

A modulation device for directing a mobile tracking device away from an asset is provided. The modulation device includes a continuous wave laser source whose output is directed at a seeker head of the mobile tracking device. The modulation device causes the generation of localized sources within the mobile tracking device and confuses the mobile tracking device as to the true location of the asset. A portable cutting device is disclosed. The portable cutting device may include a portable power supply and a laser source. The portable power supply and laser source of the portable cutting device may be positioned within a backpack and carried by a user. A handheld unit which is coupled to the laser source may be supported by the hands of the operator. The handheld unit provides power generated by the laser source to a barrier to be cut.

20 Claims, 33 Drawing Sheets

(51) Int. Cl.
*A61K 31/7105* (2006.01)
*C12Q 1/68* (2006.01)
*C12Q 1/70* (2006.01)

(56) References Cited

U.S. PATENT DOCUMENTS

| | | | |
|---|---|---|---|
| 4,177,580 A | 12/1979 | Marshall et al. | |
| 4,575,786 A | 3/1986 | Roberts | |
| 4,580,557 A | 4/1986 | Hertzmann | |
| 4,838,167 A | 6/1989 | Prahauser et al. | |
| 5,198,607 A | 3/1993 | Livingston et al. | |
| 5,272,716 A | 12/1993 | Soltz et al. | |
| 5,319,434 A | 6/1994 | Croteau et al. | |
| 5,339,328 A | 8/1994 | Miura | |
| 5,396,506 A | 3/1995 | Ball | |
| 5,401,171 A | 3/1995 | Paghdiwala | |
| 5,501,680 A | 3/1996 | Kurtz et al. | |
| 5,549,477 A | 8/1996 | Tran et al. | |
| 5,574,458 A | 11/1996 | Tran | |
| 5,600,434 A | 2/1997 | Warm et al. | |
| 5,635,905 A | 6/1997 | Blackburn et al. | |
| 5,662,291 A * | 9/1997 | Sepp et al. | 244/3.13 |
| 5,694,408 A | 12/1997 | Bott et al. | |
| 5,780,807 A | 7/1998 | Saunders | |
| 5,793,476 A | 8/1998 | Laakmann et al. | |
| 5,862,278 A | 1/1999 | Brauch et al. | |
| 5,927,648 A * | 7/1999 | Woodland | 244/118.1 |
| 6,167,075 A | 12/2000 | Craig et al. | |
| 6,187,213 B1 | 2/2001 | Smith et al. | |
| 6,269,617 B1 | 8/2001 | Blanchard | |
| 6,359,710 B1 | 3/2002 | Takken et al. | |
| 6,429,446 B1 | 8/2002 | Labaugh | |
| 6,439,888 B1 | 8/2002 | Boutoussov et al. | |
| 6,587,486 B1 | 7/2003 | Sepp et al. | |
| 6,593,540 B1 | 7/2003 | Baker et al. | |
| 6,665,079 B1 | 12/2003 | Tocci et al. | |
| 6,670,222 B1 | 12/2003 | Brodsky | |
| 6,700,094 B1 | 3/2004 | Kuntze | |
| 6,703,582 B2 | 3/2004 | Smart et al. | |
| 6,773,119 B2 | 8/2004 | Kimura et al. | |
| 6,801,550 B1 | 10/2004 | Snell et al. | |
| 6,903,674 B2 | 6/2005 | Hoesel et al. | |
| 6,933,877 B1 | 8/2005 | Halladay et al. | |
| 6,969,845 B2 | 11/2005 | von Rosenberg, Jr. | |
| 6,977,598 B2 | 12/2005 | Longbottom | |
| 7,017,467 B1 | 3/2006 | Monroe | |
| 7,053,812 B2 | 5/2006 | Trainor | |
| 7,154,591 B2 | 12/2006 | Muenter et al. | |
| 7,378,626 B2 * | 5/2008 | Fetterly | 244/3.1 |
| 7,397,014 B2 | 7/2008 | Hart et al. | |
| 7,425,916 B2 | 9/2008 | Stevens, Jr. | |
| 7,540,227 B2 | 6/2009 | McCant, Jr. | |
| 7,583,715 B2 | 9/2009 | Hill et al. | |
| 7,683,310 B1 | 3/2010 | Sinclair et al. | |
| 7,903,704 B2 | 3/2011 | Patel et al. | |
| 8,202,268 B1 | 6/2012 | Wells et al. | |
| 2002/0190162 A1 | 12/2002 | McDonnell | |
| 2005/0104731 A1 | 5/2005 | Park | |
| 2005/0200705 A1 | 9/2005 | Nieto | |
| 2006/0000988 A1 | 1/2006 | Stuart et al. | |
| 2006/0159440 A1 | 7/2006 | Purkayastha et al. | |
| 2006/0218410 A1 | 9/2006 | Robert et al. | |
| 2007/0034615 A1 | 2/2007 | Kleine | |
| 2007/0169616 A1 | 7/2007 | Vickroy | |
| 2007/0293850 A1 | 12/2007 | Stolz et al. | |
| 2008/0144673 A1 | 6/2008 | Gapontsev | |
| 2009/0091738 A1 | 4/2009 | Morcom | |
| 2009/0092157 A1 | 4/2009 | Gapontsev | |
| 2009/0224958 A1 | 9/2009 | Aphek et al. | |
| 2010/0076475 A1 | 3/2010 | Yates et al. | |
| 2010/0176097 A1 | 7/2010 | Zhu | |
| 2010/0183037 A1 | 7/2010 | Furuya et al. | |
| 2011/0024403 A1 | 2/2011 | Bradley et al. | |
| 2011/0024405 A1 | 2/2011 | Bradley et al. | |
| 2011/0113949 A1 | 5/2011 | Bradley | |

OTHER PUBLICATIONS

Bruno Crépy et al, Laser source for DIRCM at CILAS. Proc. SPIE 7483, Technologies for Optical Countermeasures VI, 74830G (Sep. 25, 2009).*
Sijan, Development of Military Lasers for Optical Countermeasures in the Mid-IR, Proc. SPIE 7483, Technologies for Optical Countermeasures VI, (Sep. 18, 2009).*
Galvanauskas et al., "KW-Power Fiber Lasers with Single Transverse Mode Output," Sep. 22, 2005, 5 pgs., downloaded from http://www.nufern.com/whitepaper_detail.php/30.
Peavey et al., "Comparison of Cortical Bone Ablations by Using Infrared Laser Wavelengths 2.9 to 9.2 µm," Lasers in Surgery and Medicine, vol. 26, pp. 421-434, 1999.
Valentine, "COTS laser technology targets emerging battlefield threats," RF Design, Nov. 29, 2007, 2 pgs., downloaded on Jun. 27, 2009 from www.printthis.clickabilityt.com/pt/cpt?action=cpt&title=COTTS+Laser+Technology+.
Waarts et al., "Fiber Lasers at JDS Uniphase," Fiber Lasers: Technology, Systems, and Applications, Proc. of Society of Photo-Opitcal Instrumentation Engineers, 2004, vol. 5335, 12 pgs.
Brown, J.M., "Digital Model of a Generic Infrared Tracker," Thesis in partial fulfillment of requirements for Master of Science in Electrical Engineering, May 1992, cover and pp. i-vii, 1-26, and 66-71 (available in Library of Rose Hillman Institute of Technology), Indiana.
Dornheim, M.A., "Cost of Protection," Aviation Week, 2008, 2 pgs., downloaded from website http://aviationweek.com/aw/generic/story_generic.jsp?channel=awst&id=news/11145p3.xml.
globalsecurity.org, "Large Aircraft Infrared Countermeasures (LAIRCM)," 3pgs., downloaded from http://ww.globalsecurity.org/military/systems/aircraft/systems/laircm.htmDec. 9, 2008.
Matthews, W., "New Angle on Missile Defense; U.S. Overcomes Cost Obstacles With UAV-based Infrared Sensor," Defense News, Sep. 29, 2008, 3 pgs., downloaded Dec. 5, 2008 from http://www.defensenews.com/story.php?i=3746183.
Northrop Grumman Corporation, "AN/AAQ-24(V) Nemesis; In Production, Deployed and Tailored to Any Platform," 2 pgs.
Northrop Gritmman Corporation, "AN/AAQ-28(V) Litening AT; Low Risk, Next Generation Targeting Pod," 2 pgs.
Northrop Grumman Corporation, "AN/AAR-54(V) Missile Warning System; Available Now for Transport, Fighter and Rotary Wing Aircraft," 2 pgs.
Osborn, K., "Army looks to field laser jammer by 2010," Army Times, May 12, 2007, 2 pgs., downloaded from http://www.armtimes.com/new/2007/05/defense_bae_jammer_070511a/12/5/2008.
Raytheon Company, "Scorpion Aircraft Protection System; Lightweight, Cost-Effective Missile Protection for Tactical Aircraft," 2006, 2 pgs.
Thermotek, Inc., "Solid State Recirculating Chiller T255P," 2 pgs.
"New Technology Aimed at Stopping Movie Piracy", downloaded from www.getthebigpicture.net, Sep. 22, 2009, 2 pgs.

* cited by examiner

HIGH POWER LASER SYSTEM

RELATED APPLICATIONS

This application is a divisional application of U.S. patent application Ser. No. 12/778,643, filed May 12, 2010 which is a continuation-in-part application of U.S. patent application Ser. No. 12/511,056, filed Jul. 28, 2009, the disclosures of which are expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon.

BACKGROUND OF THE INVENTION

The present invention relates generally to a modulation device which causes a mobile tracking device to not approach closer to an asset and to devices for cutting an object, and more particularly, to a modulation device which directs the mobile tracking device away from the asset or disables the tracking device and to portable devices which are capable of breaching a barrier.

Presently, a multitude of mobile tracking devices are known which identify an asset and attempt to move closer to the asset and potentially contact the asset. Examples of mobile tracking devices include infrared based mobile tracking devices which examine the infrared energy which is emitted by the asset and detected by the mobile tracking device. These infrared mobile tracking devices alter their direction of travel to track the highest infrared energy being detected within their field of view. Such mobile tracking devices may rely on a non-imaging detection system or an imaging detection system.

There are several devices available to misdirect a mobile infrared tracking device away from an asset. One exemplary device is infrared hot bodies which appear brighter to the mobile infrared tracking device than the asset. These infrared hot bodies may be expelled by the asset. The mobile tracking device detects the brighter infrared hot bodies and follows the hot bodies as they become further spaced apart from the asset; thereby directing the mobile infrared tracking device away from the asset. Exemplary infrared hot bodies include flares.

Another type of device is a laser device which directs a pulsed or modulated laser signal at a detection system of the mobile tracking device. The pulsed or modulated laser signal is tailored to the specific characteristics of the mobile tracking device. An example of one device which is tailored to multiple types of tracking devices is disclosed in U.S. Pat. No. 6,359,710.

Often times law enforcement, military personnel, fire personnel, and other types of rescue personnel need to open or otherwise cross a barrier. Exemplary barriers include doors, walls, and other impediments to advancement. Often times this requires the barrier to be altered to permit passage.

Often these personnel are working in confined areas and do not have access to large units which can assist in the breaching of a barrier. A need exists for a portable unit which can be carried by a person and which is capable providing enough power to effectively breach a barrier.

SUMMARY OF THE INVENTION

In an exemplary embodiment of the present disclosure, a modulation device is disclosed. In another exemplary embodiment, a method of interacting with a mobile tracking device is disclosed. In yet another exemplary embodiment of the present disclosure, a portable cutting device is disclosed. In still another exemplary embodiment of the present disclosure, a method of using a portable cutting device is disclosed.

In another exemplary embodiment of the present disclosure, an apparatus for interacting with a mobile tracking device is provided. The apparatus comprising a body; at least one propulsion device supported by the body; a plurality of sensor modules supported by the body which monitor the environment surrounding the body; a controller operatively connected to the plurality of sensor modules, the controller determining a presence of the mobile tracking device in the environment surrounding the body based on information collected by the plurality of sensor modules and a current location of the mobile tracking device; and a modulation system which receives the current location of the mobile tracking device from the controller, orients a tracking system of the modulation system based on the current location of the mobile tracking device, detects the mobile tracking device, updates the location of the mobile tracking device, and directs a continuous beam of optical energy at the mobile tracking device. The continuous beam of optical energy being produced by a plurality of semiconductor lasers whose output are combined.

In yet another exemplary embodiment of the present disclosure, a portable cutting device for transport by a human operator is provided. The portable cutting device comprising a laser source which provides optical energy, the laser source being a plurality of continuous wave semiconductor lasers whose output is combined to provide the optical energy; a battery power source; a laser directing device supporting focusing optics in a collimating chamber, the focusing optics focus the optical energy provided by the laser source; at least one storage container, the at least one storage container housing the laser source and the battery power source; and at least one flexible optical conduit extending from an interior of the at least one storage container to the laser directing device, the at least one flexible optical conduit communicating the optical energy produced by the laser source to the laser directing device.

BRIEF DESCRIPTION OF THE DRAWINGS

The foregoing aspects and many of the attendant advantages of this invention will become more readily appreciated as the same become better understood by reference to the following detailed description when taken in conjunction with the accompanying drawings.

FIG. 8 illustrates a processing sequence for charging the battery source of the modulation device;

Figure 1:
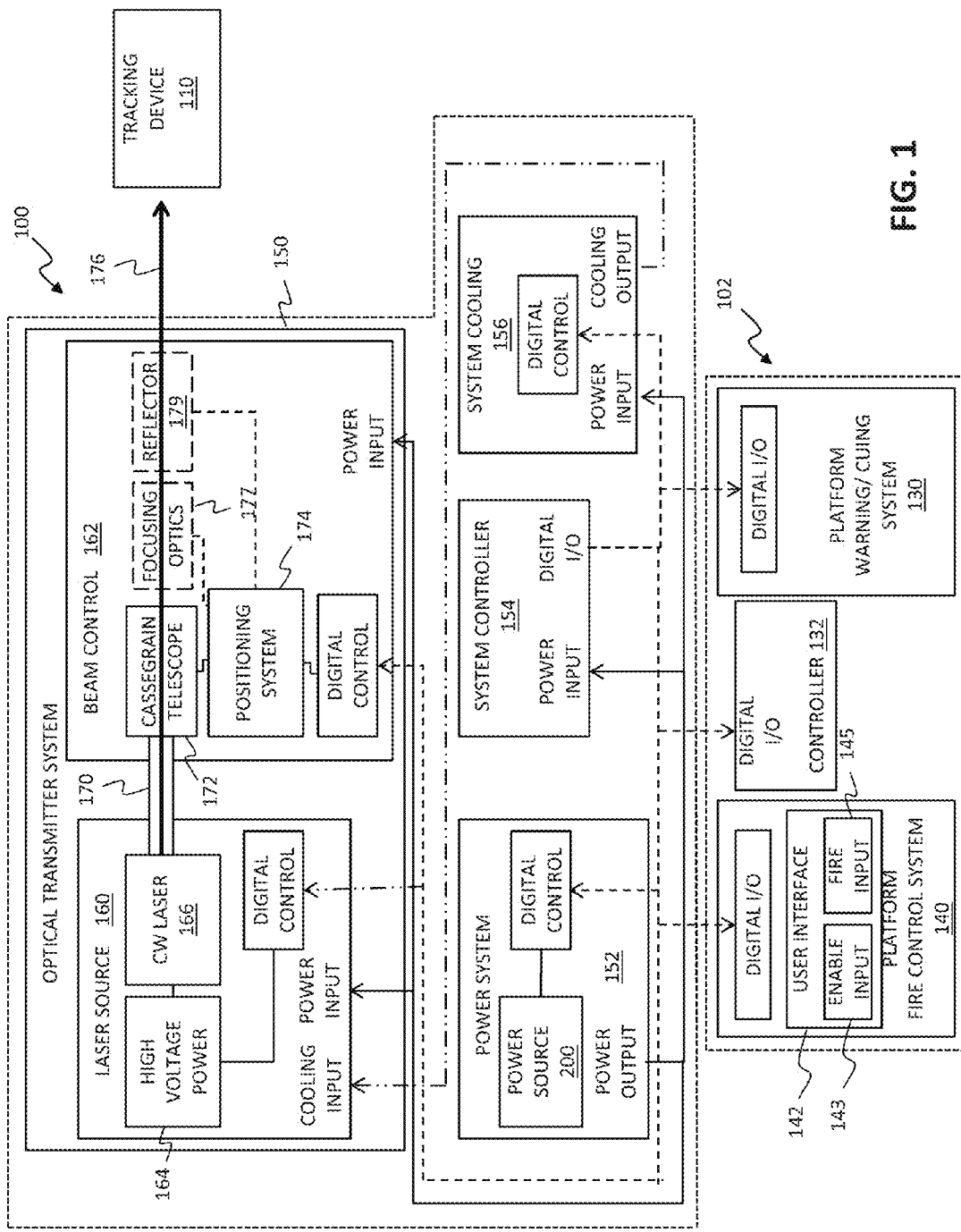
FIG. 1 illustrates a representative view of a modulation device and associated asset.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates embodiments of the invention, and such exemplifications are not to be construed as limiting the scope of the invention in any manner.

DETAILED DESCRIPTION OF THE DRAWINGS

For the purposes of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

The present disclosure is directed to modulation devices which are implemented to protect aircraft, such as commercial airlines and military aircraft. However, the principles discussed herein are applicable to other types of assets. Exemplary assets include moveable assets, such as aircraft, ships, buses, or trucks, or land based assets, such as an airport, factory, building, or facility. Exemplary modulation devices include countermeasure devices.

Referring to FIG. 1, a modulation device 100 is shown. Modulation device 100 is coupled to an asset 102. For purposes of discussion, asset 102 is considered to be an airplane, such as the airplane designated 102 in FIG. 2. However, the present disclosure is contemplated for use with a multitude of different assets. Airplane 102 includes a body or fuselage 104, a pair of main wings 105, tail wings 106, and a plurality of propulsion devices 108. Exemplary propulsion devices include jet engines, internal combustion engines with associated propellers, and any other suitable engine arrangement.

Figure 3:
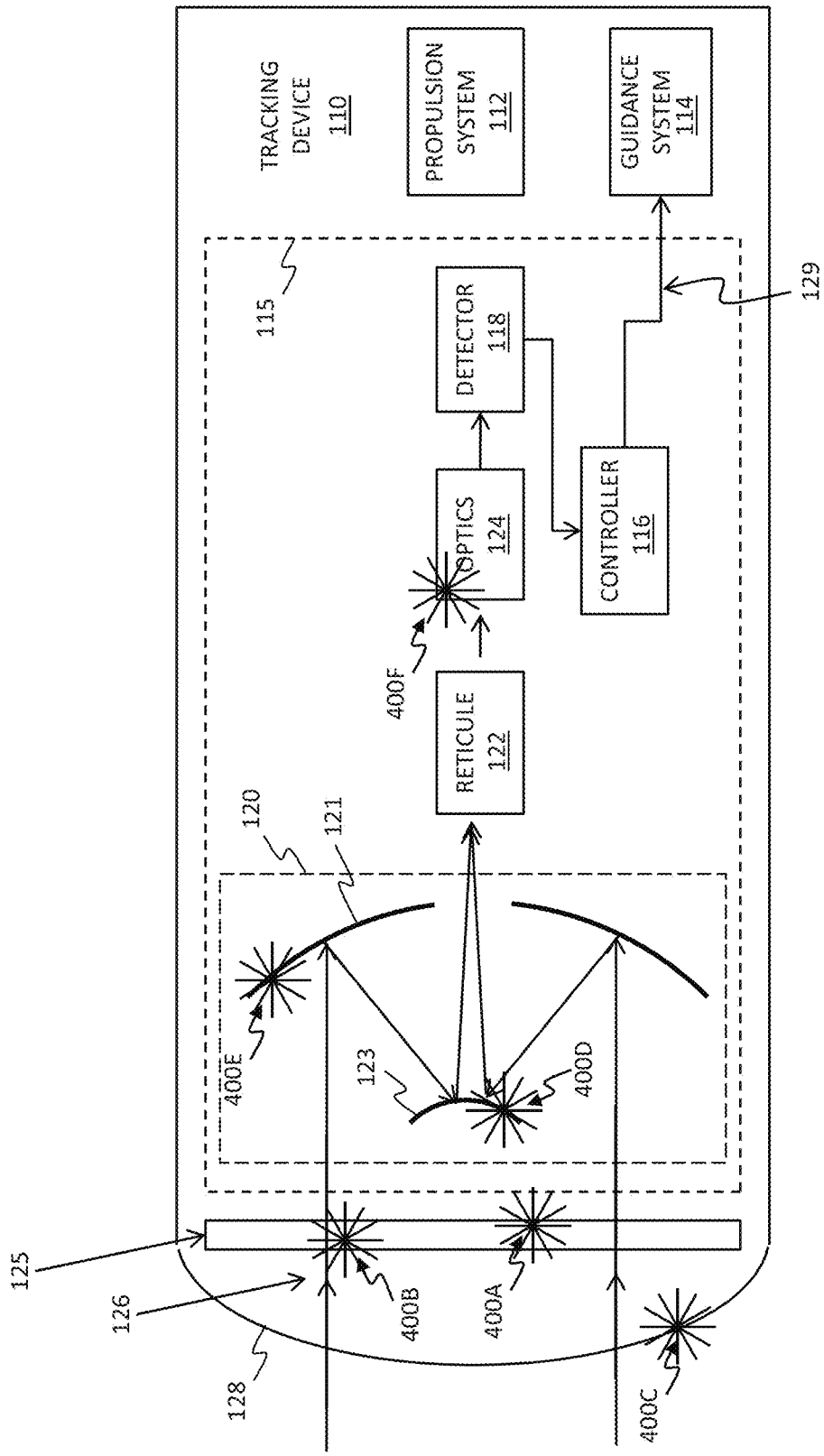
FIG. 3 illustrates an exemplary mobile tracking device.

Referring to FIG. 3, components of a mobile tracking device 110 are shown. Mobile tracking device 110 includes a propulsion system 112 which provides power to propel mobile tracking device 110. Exemplary propulsion systems include solid fuel rockets, engines, and any other suitable devices for providing power to mobile tracking device 110. Mobile tracking device 110 also includes a guidance system 114 which controls the direction of travel of mobile tracking device 110. Exemplary guidance system components include wings for an airborne mobile tracking device 110, a rudder for a marine mobile tracking device 110, and ground engaging members for a land based mobile tracking device 110. The guidance system 114 steers mobile tracking device 110 to change a direction of travel of mobile tracking device 110. Exemplary airborne tracking devices include rockets, airplanes, and other flying devices. Exemplary marine tracking devices include boats (see FIG. 11), submersible devices, and other marine devices. Exemplary land based tracking devices include wheeled devices, tracked devices, and other suitable land based devices.

Mobile tracking device 110 includes a controller 116 which controls the operation of propulsion system 112 and guidance system 114. Mobile tracking device 110 also includes a gimbaled seeker head 115 which is able to move independent of the remainder of mobile tracking device 110. Seeker head 115 supports controller 116, a detector 118, telescope 120, a reticule 122, and optics 124.

In operation, electromagnetic radiation 126 from the environment enters an optical window 128 of mobile tracking device 110. Optical window 128 may be a dome. Optical window 128 may be selected to only pass electromagnetic radiation 126 within a certain wavelength band. For instance, in the case of an infrared mobile tracking device 110, optical window 128 may only pass electromagnetic radiation 126 within the infrared spectrum or a portion of the infrared spectrum. In other embodiments, a separate filter 125 is included somewhere within the optical setup of mobile tracking device 110 to limit the range of wavelengths of electromagnetic radiation 126 passed on to detector 118. Filter 125 is shown between optical window 128 and telescope 120. However, filter 125 may be positioned anywhere between optical window 128 and detector 118.

The electromagnetic radiation 126 is received by telescope 120. Telescope 120 includes a primary mirror 121 which focuses the electromagnetic radiation 126 towards a secondary mirror 123. Secondary mirror 123 in turn focuses the electromagnetic radiation 126 towards reticule 122. Reticule 122 spins to provide a modulated signal of the electromagnetic radiation. Optics 124 receives and focus the modulated signal of the electromagnetic radiation 126 passing through reticule 122 onto detector 118 which is a non-imaging detector.

Controller 116 receives input from detector 118 which is used by controller 116 to determine the location the brightest object in the environment, typically asset 102. The modulated signal allows controller 116 to discriminate between background electromagnetic radiation and the radiation of asset 102, as well as, determine the location of asset 102 relative to a direction of travel of mobile tracking device 110. Based on this input from detector 118, controller 116 determines a desired direction of travel for mobile tracking device 110 which corresponds to tracking device 110 heading towards asset 102. Seeker head 115 is adjusted to center the brightest object in the environment so that seeker head 115 is pointed directly at the brightest object. Controller 116 provides this adjustment of seeker head 115 (from its intended orientation in line with the direction of travel of mobile tracking device 110) to guidance system 114 as error signal 129. Guidance system 114 uses this error signal 129 to alter the direction of travel of mobile tracking device 110. Over time, if mobile tracking device 110 is tracking asset 102 mobile tracking device 110 will be pointed at asset 102 and seeker head 115 generally produces a small error signal which is indicative of mobile tracking device 110 being aligned to intercept asset 102.

In the embodiment illustrated in FIG. 3, mobile tracking device 110 includes a spinning reticule 122. In another embodiment, mobile tracking device 110 does not include reticule 122 but rather secondary mirror 123 is tilted and telescope 120 is spun to produce a signal for controller 116. In one embodiment, detector 118 is an imaging detector and controller 116 processes the images from detector 118 to determine the location of asset 102.

Returning to FIG. 2, airplane 102 includes warning/cuing system 130 which detects when a mobile tracking device 110 has been launched and/or is tracking airplane 102. Warning/cuing system 130 includes sensor modules 131 which monitor the environment around airplane 102. Illustratively, four sensor modules 131A-D are shown. Depending on the asset 102 being protected, fewer or additional sensor modules 131 may be used. In one embodiment, sensor modules 131 include focal plane array sensors with wide field of views that continuously survey the environment for mobile tracking devices 110. In one embodiment, warning/cuing system 130 looks for a characteristic signal that indicates the launch of an airborne mobile tracking device 110. In the case of airborne mobile tracking device 110, the mobile tracking device 110 has a characteristic infrared and ultraviolet signature which warning/cuing system 130 recognizes as an airborne mobile tracking device 110.

Exemplary warning/cuing systems are disclosed in U.S. patent application Ser. No. 12/541,772 ,filed Aug. 14, 2009, the disclosure of which is expressly incorporated by reference herein. As explained herein, warning/cuing system 130 communicates with modulation device 100. Modulation device 100, in turn, provides optical energy from a continuous wave laser to redirect mobile tracking device 110 from tracking the path of asset 102 or to disable mobile tracking device 110. In one embodiment, warning/cuing system 130 is provided as part of modulation device 100 instead of as a separate component of airplane 102.

Airplane 102 further includes a fire control system 140. Fire control system 140 interprets information provided by warning/cuing system 130 and provides a user interface 142 through which the operator of asset 102 activates modulation device 100. In one embodiment, user interface 142 includes a user input 143 to enable modulation device 100 and a user input 145 to permit modulation device 100 to fire. In one embodiment, modulation device 100 is automatically activated when asset 102 is moving. Exemplary inputs include switches, buttons, and other suitable types of user inputs.

Returning to FIG. 1, modulation device 100 is represented. Modulation device 100 includes an optical transmitter system 150, a power system 152, a system controller 154, and a cooling system 156. Each of optical transmitter system 150, power system 152, and cooling system 156 are coupled to system controller 154. System controller 154 receives input from and provides instructions to each of optical transmitter system 150, power system 152, and cooling system 156 to control the operation of modulation device 100. As explained herein, in one embodiment, modulation device 100 is housed in a self-contained pod which may be coupled to asset 102.

Optical transmitter system 150 includes a laser source module 160 and a beam control module 162. Laser source module 160 includes a high voltage power supply 164 which receives power from power system 152. High voltage power supply 164 drives a continuous wave laser 166. In one embodiment, continuous wave laser 166 is a continuous wave fiber laser. In one embodiment, continuous wave laser 166 is a continuous wave Ytterbium single mode fiber laser. Details regarding an exemplary continuous wave laser 166 are provided in U.S. patent application Ser. No. 11/973,437 ,titled POWERFUL FIBER LASER SYSTEM, assigned to IPG Photonics Corporation, the disclosure of which is expressly incorporated by reference herein. Details regarding an exemplary continuous wave laser 166 are provided in U.S. patent application Ser. No. 11/611,247 ,titled FIBER LASER WITH LARGE MODE AREA FIBER, assigned to IPG Photonics Corporation, the disclosure of which is expressly incorporated by reference herein. In one embodiment, continuous wave laser 166 is a solid state laser. Other exemplary continuous wave lasers include a 2.0 micrometer (μm) Thulium Fiber Laser (1.96-2.2 (μm) Thulium laser) having an output power of about at least 1 kW and a 1.0 μm, 800 Watt Direct Diode. An exemplary Thulium fiber laser is disclosed in U.S. Pat. No. 6,801,550 ,the disclosure of which is expressly incorporated by reference herein.

Figure 4:
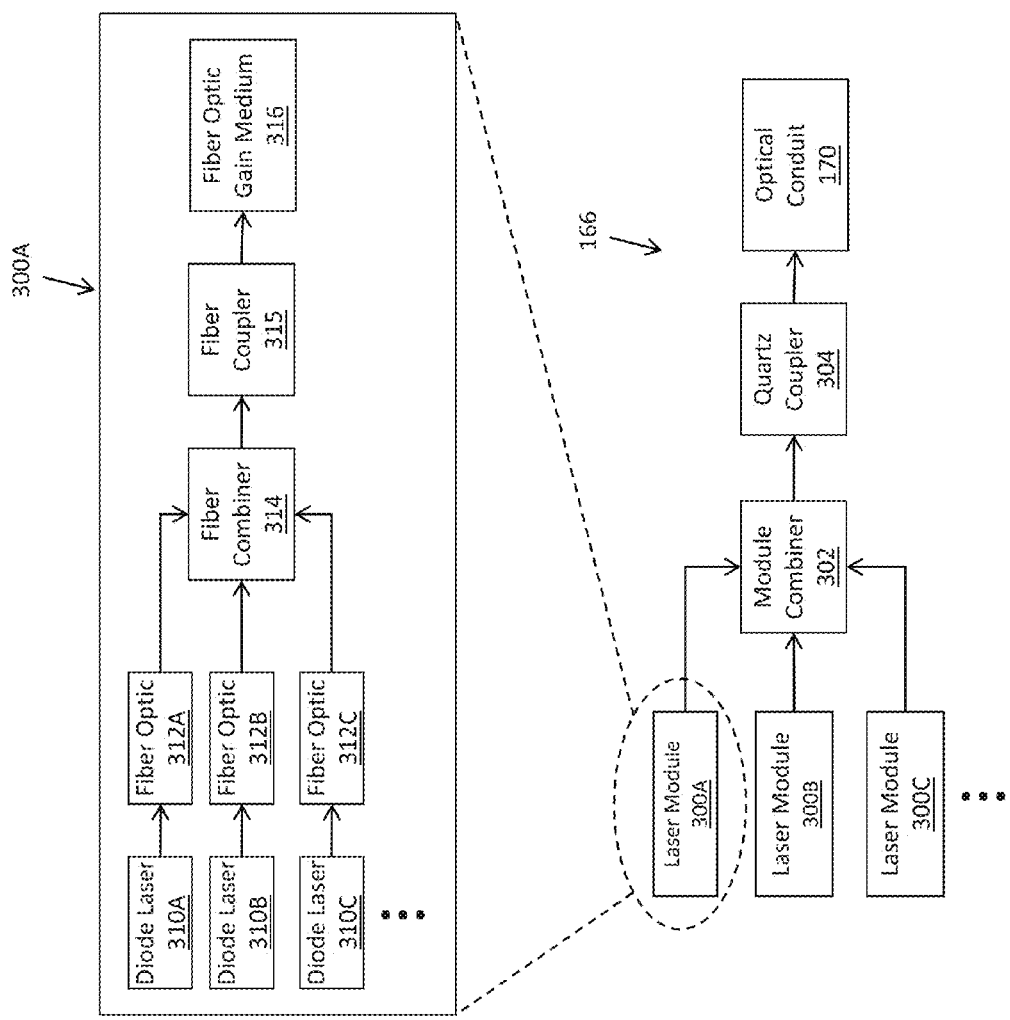
FIG. 4 illustrates an exemplary laser source.

Referring to FIG. 4, an exemplary configuration of continuous wave laser 166 is shown. Continuous wave laser 166 includes a plurality of individual modules 300 each of which provide a single mode 1.07 μm output beam. The output of each of modules 300 is combined together through a module combiner 302 which brings the energy together in a single beam. This combined beam is coupled to an optical conduit 170 through a quartz coupler 304. Although three laser modules 300 are illustrated, any number of laser modules 300 may be included.

The components of a given laser module 300 are also shown in FIG. 4. The laser module 300 includes a plurality of diode lasers 310 each of which are coupled into a respective Ytterbium fiber 312. The output of the Ytterbium fibers 312 are combined through a fiber combiner 314 which brings the energy together. This energy is fed through a coupler 315 into an Ytterbium fiber optic gain medium 316 which produces therefrom a single mode 1.07 μm output beam. Although three diode laser sets 310 are illustrated any number of diode laser sets 310 may be included.

In one embodiment, the power of continuous wave laser 166 is about 3 kilowatts (kW). In one embodiment, the power level of continuous wave laser 166 is about 5 kW. In one embodiment, the power level of continuous wave laser 166 is about 10 kW. In one embodiment, the power level of continuous wave laser 166 is about 20 kW. In one embodiment, the power level of continuous wave laser 166 is about 50 kW. In one embodiment, the power level of continuous wave laser 166 is between about 3 kW and 20 kW. In one embodiment, the power level of continuous wave laser 166 is at least 3 kW. In one embodiment, the power level of the continuous wave laser 166 is at least 3 kW for a duration of at least about 11 minutes.

Returning to FIG. 1, the optical energy produced by continuous wave laser 166 is communicated to beam control module 162 through optical conduit 170. An exemplary optical conduit 170 is a fiber optic cable.

Beam control module 162 includes a beam expander 172 and a positioning system 174. Beam expander 172 receives the optical energy from optical conduit 170 and provides a generally collimated beam 176 of optical energy which exits modulation device 100. An exemplary beam expander is a Cassegrain telescope. Optical energy from optical conduit 170 is provided at a focus of the Cassegrain telescope which then generally collimates this optical energy to produce the expanded beam of optical energy 176. In one embodiment, a path length of beam expander 172 may be automatically adjusted by system controller 154 to change output beam 176 from a generally collimated beam of optical energy to a focused beam of optical energy. In this case, beam expander 172 may serve both as a beam expander (collimator) and focusing optics. In one embodiment, beam control module 162 also includes separate focusing optics 177 which focus the output beam 176 at a given distance from modulation device 100.

Figure 5:
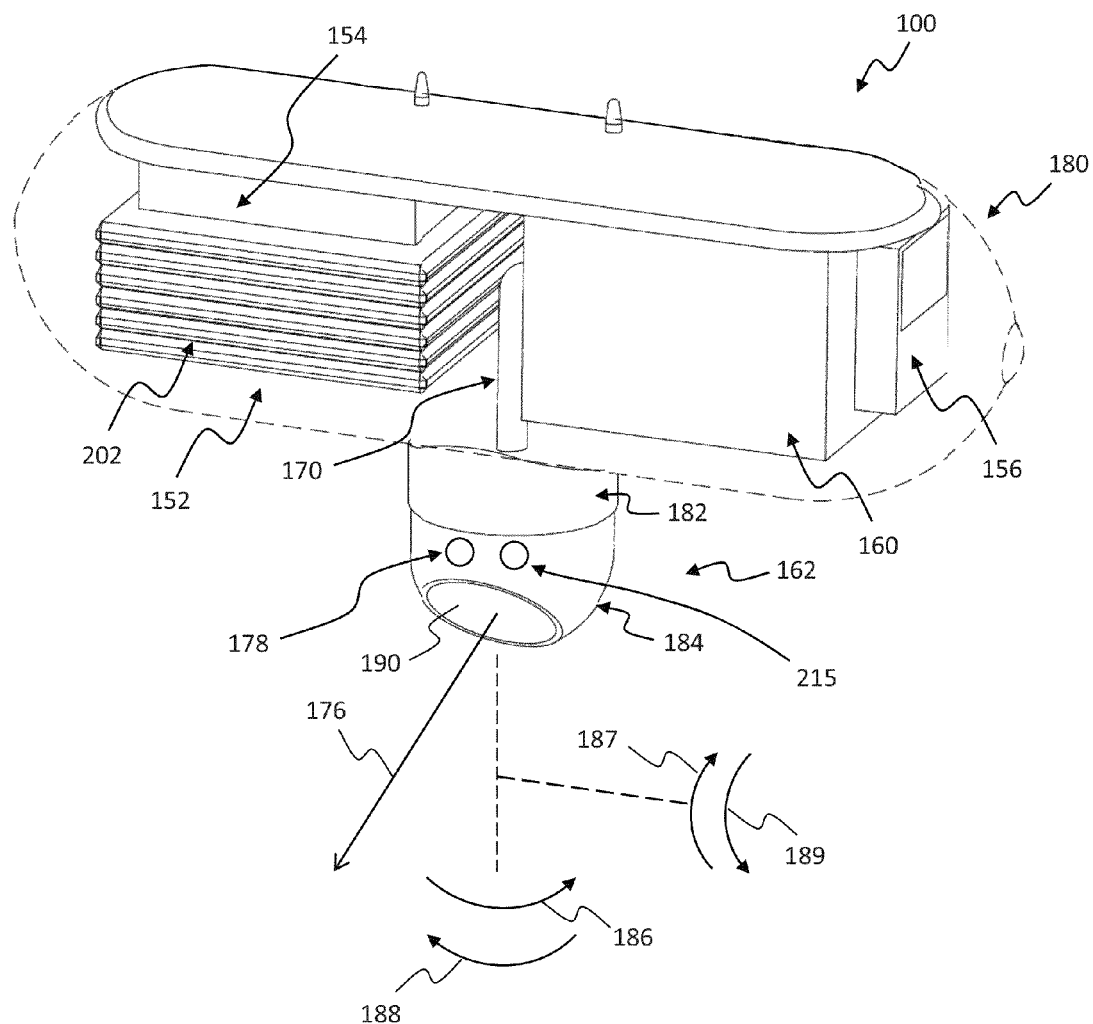
FIG. 5 illustrates a perspective view of a modulation device wherein portions of the housing are shown in phantom.

Positioning system 174 alters the direction in which collimated beam 176 is directed. Referring to FIG. 5, an exemplary configuration of modulation device 100 is shown. Modulation device 100 includes a housing 180 which houses system controller 154, power system 152, cooling system 156 and laser source module 160 of optical transmitter system 150. Provided on a lower side of housing 180 is positioning system 174. Positioning systems 174 includes a housing 182 coupled to housing 180 and a rotatable head 184 which is rotatable in directions 186 and 188. In one embodiment, the rotatable head 184 has a pointing accuracy of up to 25 microradians. Rotatable head 184 includes an optical window 190 through which output beam 176 is directed. Output beam 176 is generally a directed beam and is not radiated in all directions. In one embodiment, positioning system 174 also includes at least one reflector 179 which may be controlled to alter the direction output beam 176 in directions 187 and 189. The reflector 179 may be tilted to alter the elevation of collimated beam 176 by positioning system 174.

Figure 2:
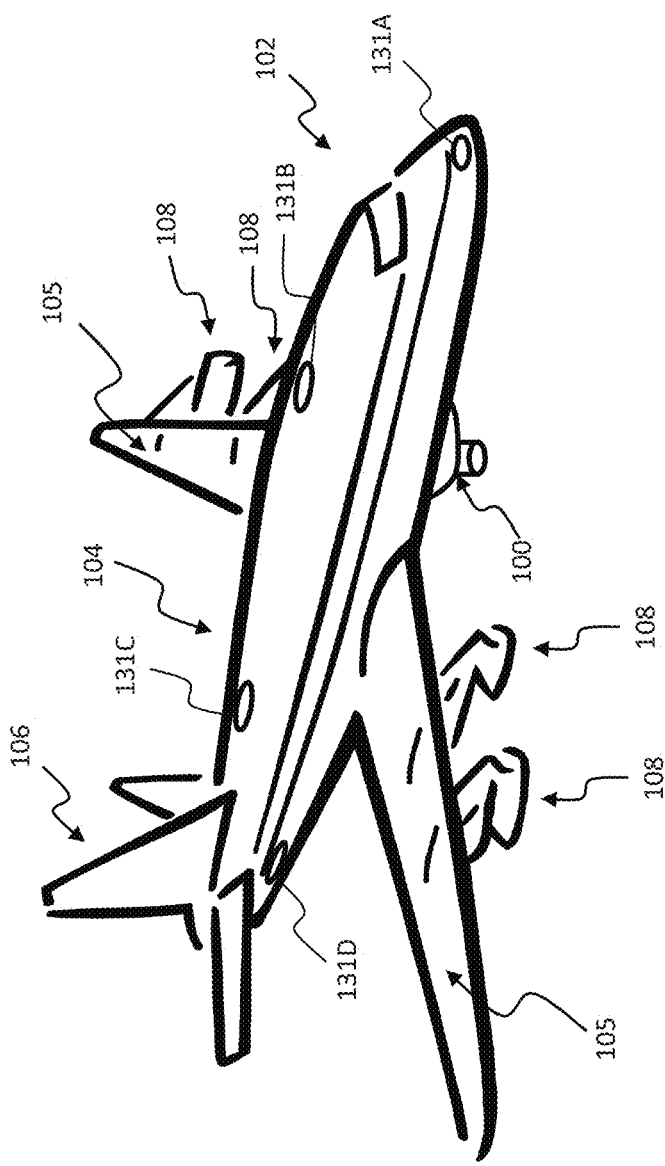
FIG. 2 is a view of a representative asset.

Housing 180, in the illustrated embodiment, is a pod which is detectably coupled to airplane 102 (see FIG. 2). Referring to FIG. 5, housing 180 includes a set of couplers 181 which cooperate with couplers 183 on asset to couple housing 180 to airplane 102. In one embodiment, housing 180 is coupled to airplane 102 by any suitable conventional mechanism which permits housing 180 to be later detached from airplane 102. Exemplary coupling systems are disclosed in U.S. patent application Ser. No. 12/541,772, filed Aug. 14, 2009, the disclosure of which is expressly incorporated by reference herein.

Returning to FIG. 1, power system 152 includes a power source 200. In one embodiment, power source 200 is a plurality of batteries. The batteries may be rechargable batteries. Exemplary rechargeable batteries include lithium-ion batteries and lithium polymer batteries. Exemplary lithium-ion batteries include commercially available cells, such as those available from A123 Systems located in Watertown, Mass. In one embodiment, a plurality of lithium-ion cells are assembled into a battery pack 202 (see FIG. 5). In one embodiment, these cells have a nominal amp-hour rating of 2.3 Ah and a nominal load voltage of 3.3 DCV/cell. Based thereon, battery pack 202 should be able to deliver 52.8 V at 2.3 amps for 1 hour. Under high load (10 C (10×5×2.3 or 115 Amps)) the voltage will "squat" to approximately 2.8 volts/cell. At this level the battery pack 202 could deliver 45 V at 115 amps (or 5 kW) for 6 min. Under severe load (20 C (20×5*2.3) or 230 amps)) the voltage would squat to approximately 2.5 volts. At this level the battery pack 202 could deliver 40 V at 230 amps (or 9 kW) for about a half minute. In one embodiment, battery pack 202 provides 28 VDC power for modulation device 100.

The use of battery pack 202 allows high power to be provided to laser source module 160 without causing a large power spike requirement in the power system of asset 102. In essence, battery pack 202 acts as a capacitor for laser source module 160.

In one embodiment, continuous wave laser 166 is a three kilowatt Yterrbium single mode fiber laser such as ones commercially available from IPG Photonics located at IPG Photonics Corporation, 50 Old Webster Road Oxford, Mass. 01540 USA and power supply 152 provides about 28 VDC. In general, commercial laser sources from IPG Photonics include an AC-to-DC converter to convert power from an AC source to DC power for continuous wave laser 166. Since power supply 152 already provides DC power, when a commercial laser source is being used for continuous wave laser 166 the AC-to-DC converter is removed and replaced with a DC driving circuit 320 (see FIGS. 6 and 7) which corresponds high voltage power supply 164. DC driving circuit 320 provides power from power supply 152 to continuous wave laser 166 and regulates the power level provided.

Figure 6:
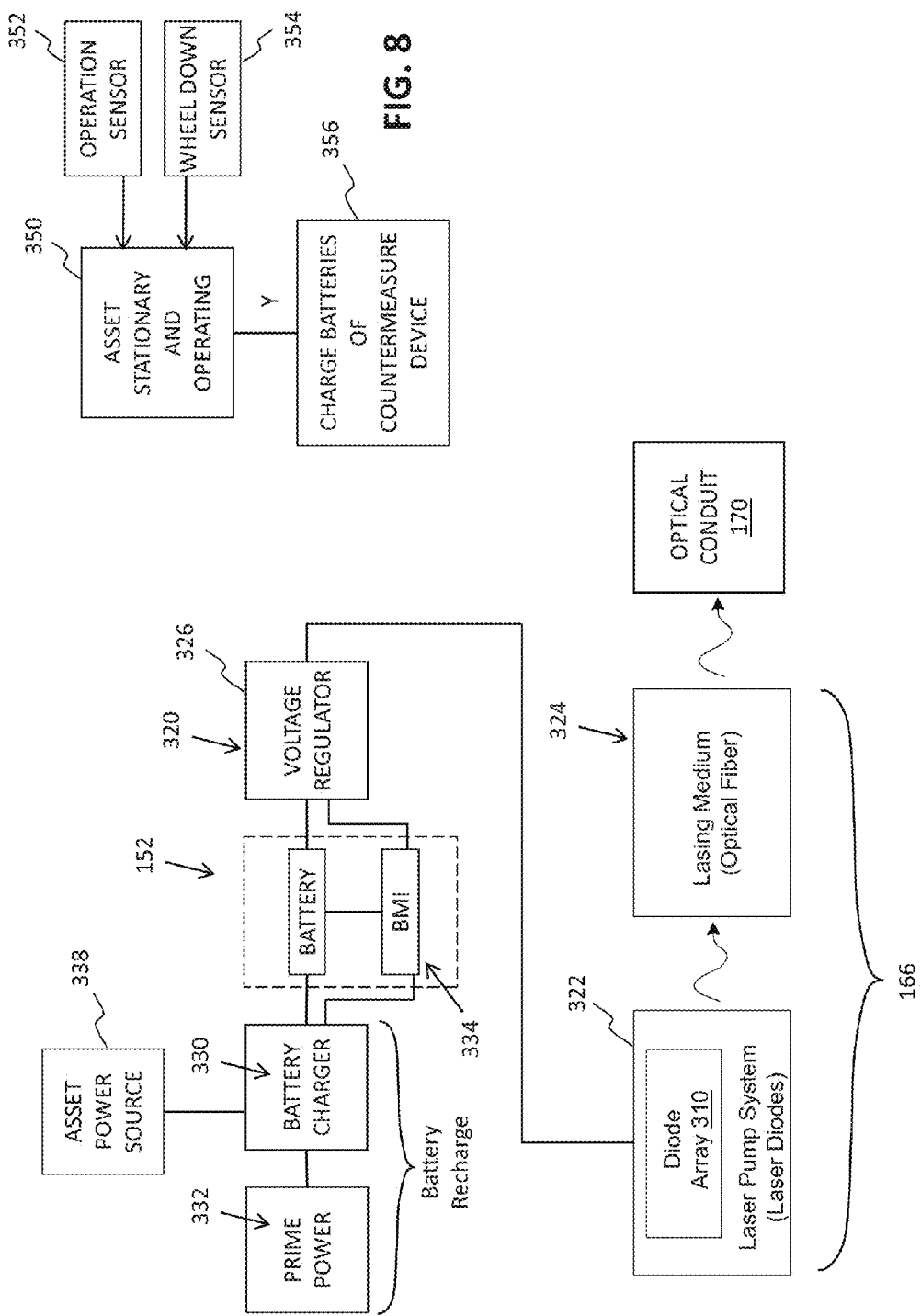
FIG. 6 illustrates a first arrangement of components of a power supply of the modulation device.
Figure 7:
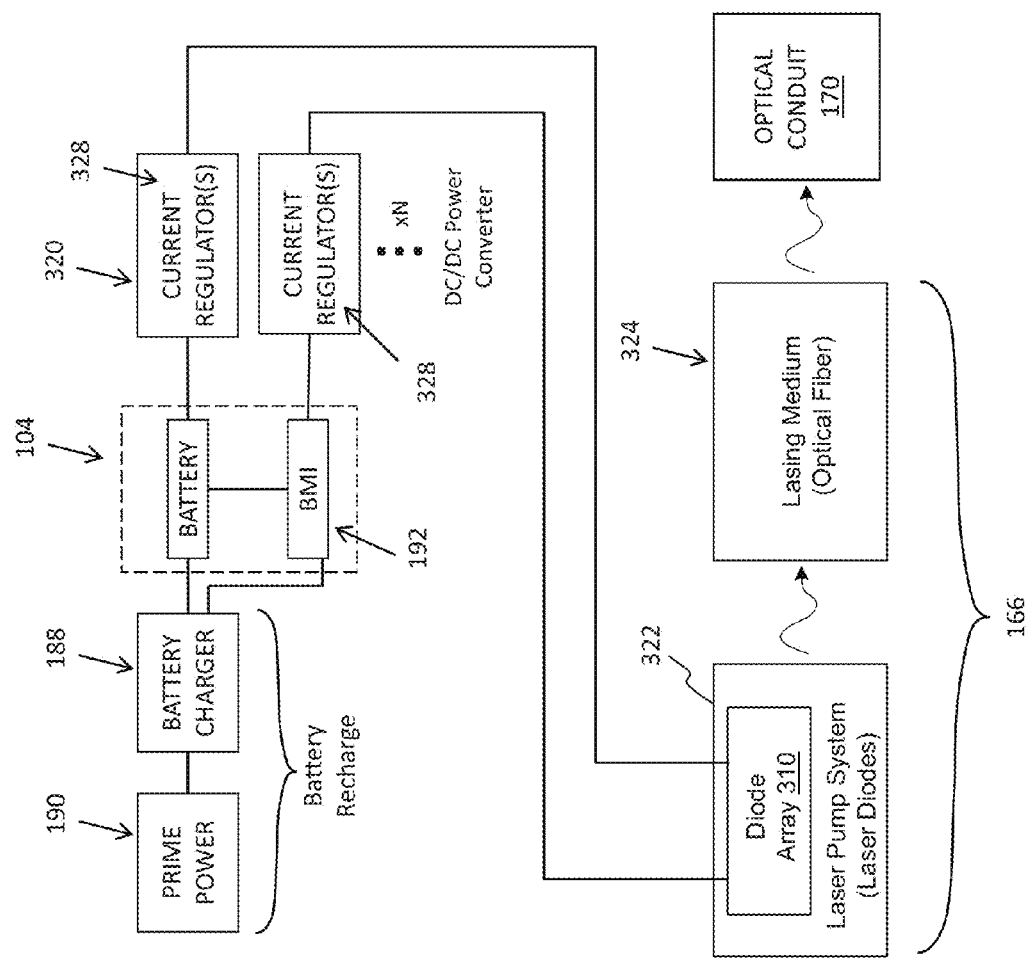
FIG. 7 illustrates a second arrangement of components of a power supply of the modulation device.

Referring to either FIG. 6 or FIG. 7, continuous wave laser 166 is represented. Continuous wave laser 166, as explained in connection with FIG. 4, includes a laser pump system 322 which includes a plurality of laser diodes 310. Laser diodes 310 provide the pump energy for the lasing medium 316 of continuous wave laser 166. The lasing medium 316 is provided as part of a fiber optical cable. The output of the lasing medium 316 is provided to optical conduit 170.

In FIG. 6, power supply 152 is coupled to laser diodes 183 through DC driving circuit 320 which includes a single voltage regulator 326 that powers laser diodes 310. In FIG. 7, power supply 152 is coupled to laser diodes 310 through DC driving circuit 320 which includes a plurality of current regulators 328. Each current regulator 328 provides the power to one of the modules 300 (see FIG. 4) to provide power to the diodes of that module 300.

Referring to either FIG. 6 or FIG. 7, power supply 152 may be charged with a battery charger 330 coupled to a prime power source 332. Battery charger 330 is contained within housing 180. Exemplary prime power sources include a standard AC wall outlet. Power supply 152 includes a battery management interface 334 which controls the recharging of the batteries with battery charger 330.

In one embodiment, power system 152 is recharged by a power source 338 of the asset 102. An exemplary power source 338 is a DC generator of asset 102. Referring to FIG. 8, a controller of asset 102 determines if asset 102 is operating and stationary (or otherwise operating at a low power level), as represented by block 350. The controller checks an operational sensor 352 to determine if asset 102 is operational. Exemplary operational sensors include engine sensors which indicate the operation of propulsion devices 108. The controller also checks in the case of an airplane 102, a wheel down sensor 354, which indicates when the landing gear of airplane 102 is lowered. If the controller determines that airplane 102 is stationary (wheels down) and operational, then the controller provides charging energy to battery charger 330, as represented by block 356. In one embodiment, airplane 102 does not need to be stationary, but rather only be operating at a low power level, such as flying at a moderate speed. In this case, the controller monitors a power load of airplane 102 and provides charging energy to battery charger 330 when the power load is below a threshold amount.

Cooling system 156 provides cooling to the other components of modulation device 100. In one embodiment, cooling system 156 provides cooling to laser source module 160. In one embodiment, cooling system 156 provides cooling to laser source module 160 and the optical components of beam control module 162. In one embodiment, cooling system 156 provides cooling fluid to power system 152, laser source module 160, and the optical components of beam control module 162. Cooling system 156 may be either air-cooled or liquid cooled. Exemplary cooling systems are provided from Thermo Tek, Inc. located at 1200 Lakeside Parkway, Suite 200 in Flower Mound, Tex.

As indicated in FIG. 1, the components of modulation device 100 are coupled to each other and to asset 102 through a digital communication system. In one embodiment, the digital communication system includes a common bus for the components within modulation device 100. Although a digital communication system is illustrated, any suitable connection is acceptable between the components, such as analog connections. In one embodiment, laser source module 160 is coupled to enable input 143 and fire input 145 through discrete connections outside of the digital communication system. Further, warning/cuing system 130 is coupled to system controller 154 through a separate communication connection. An exemplary communication connection is the MIL-STD-1553 Bus.

Figure 9:
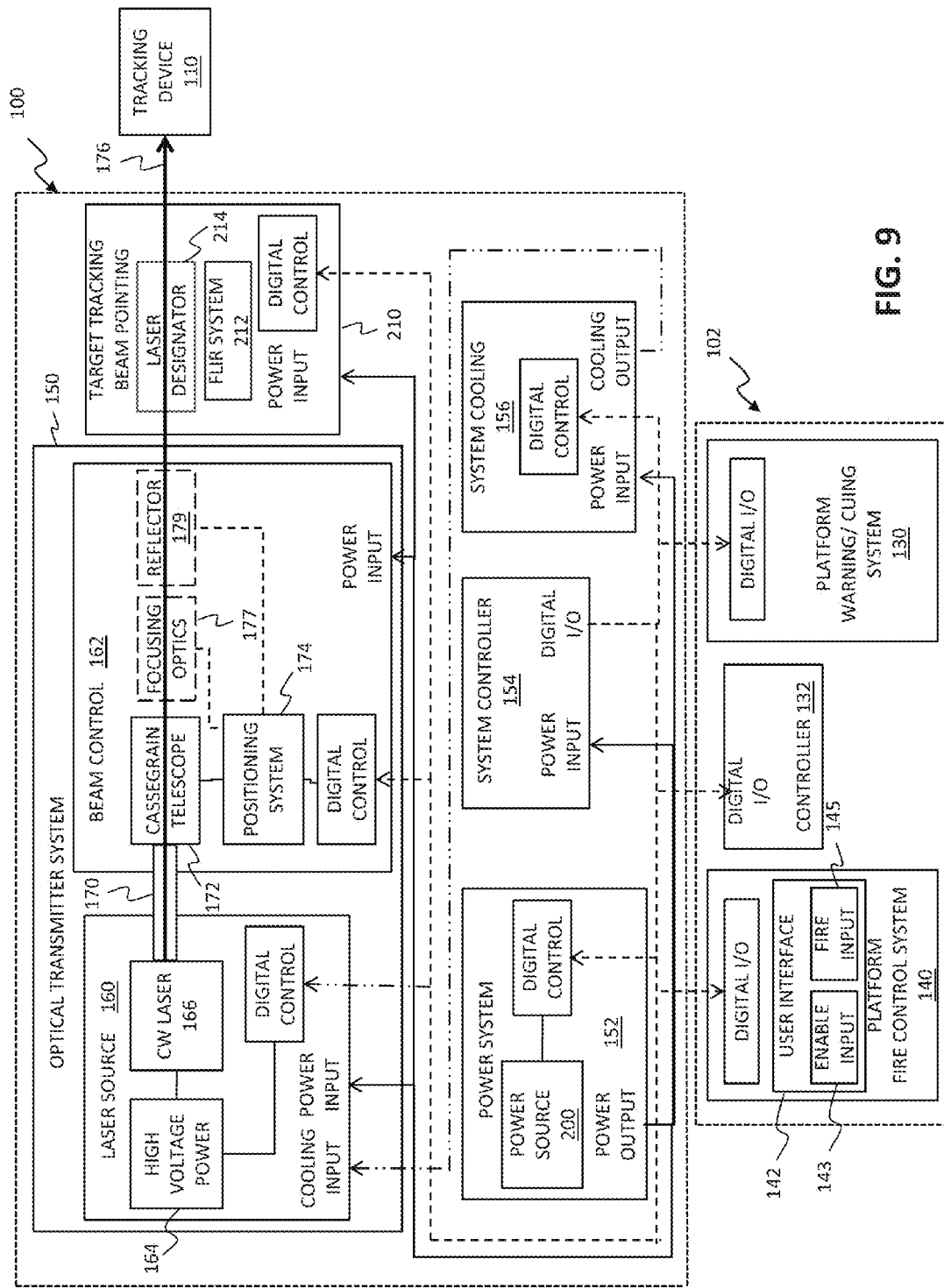
FIG. 9 illustrates a representative view of a modulation device and associated asset.

Referring to FIG. 9, in one embodiment, modulation device 100 also includes a target tracking and beam pointing system 210. Target tracking and beam pointing system 210 monitors the scene surrounding asset 102. In one embodiment, beam pointing system 210 includes a vision system, illustratively a FLIR system 212, which provides images of the scene surrounding asset 102. FLIR system 212, illustratively, has a separate optical window 178 through which the vision system monitors the location of mobile tracking device 110. In one embodiment, FLIR system 212 uses the same optical window 190 as output beam 176 and is bore sighted to output beam 176.

Figure 10A:
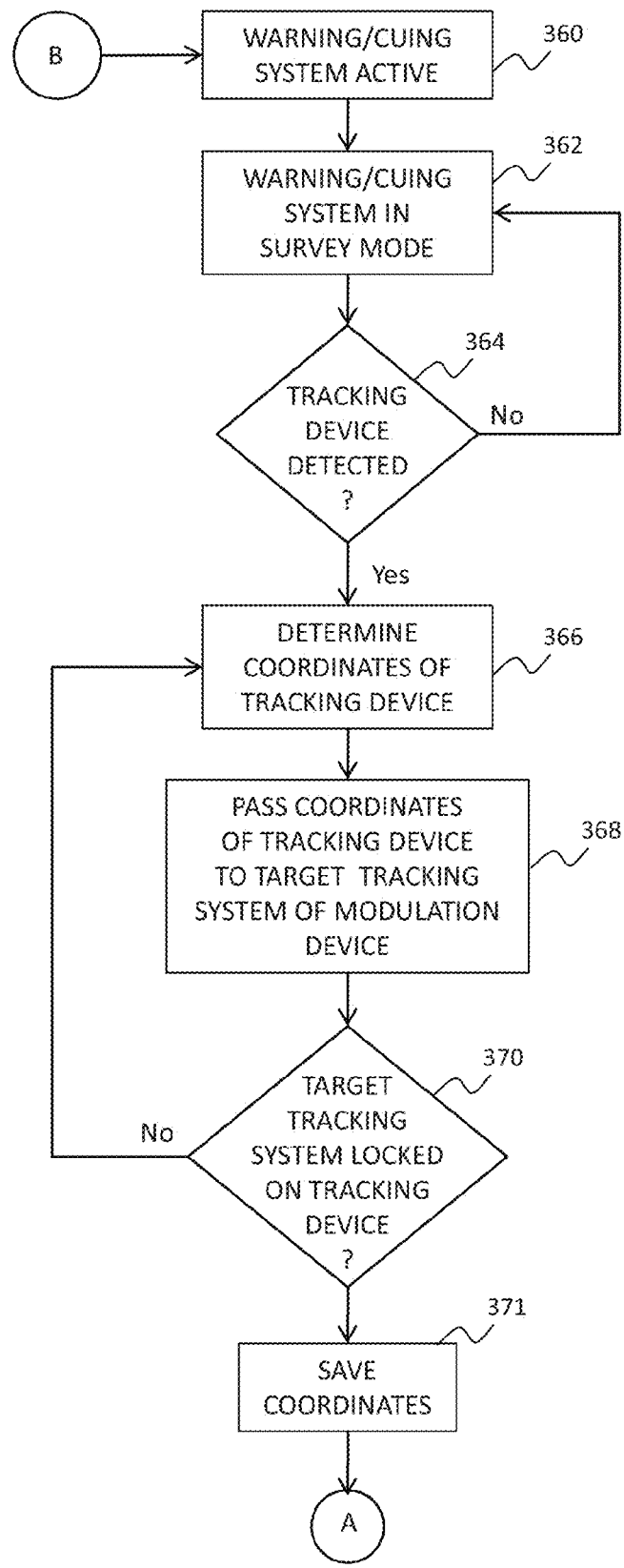
FIGS. 10A and 10B illustrate a processing sequence for engaging a mobile tracking device.
Figure 10B:
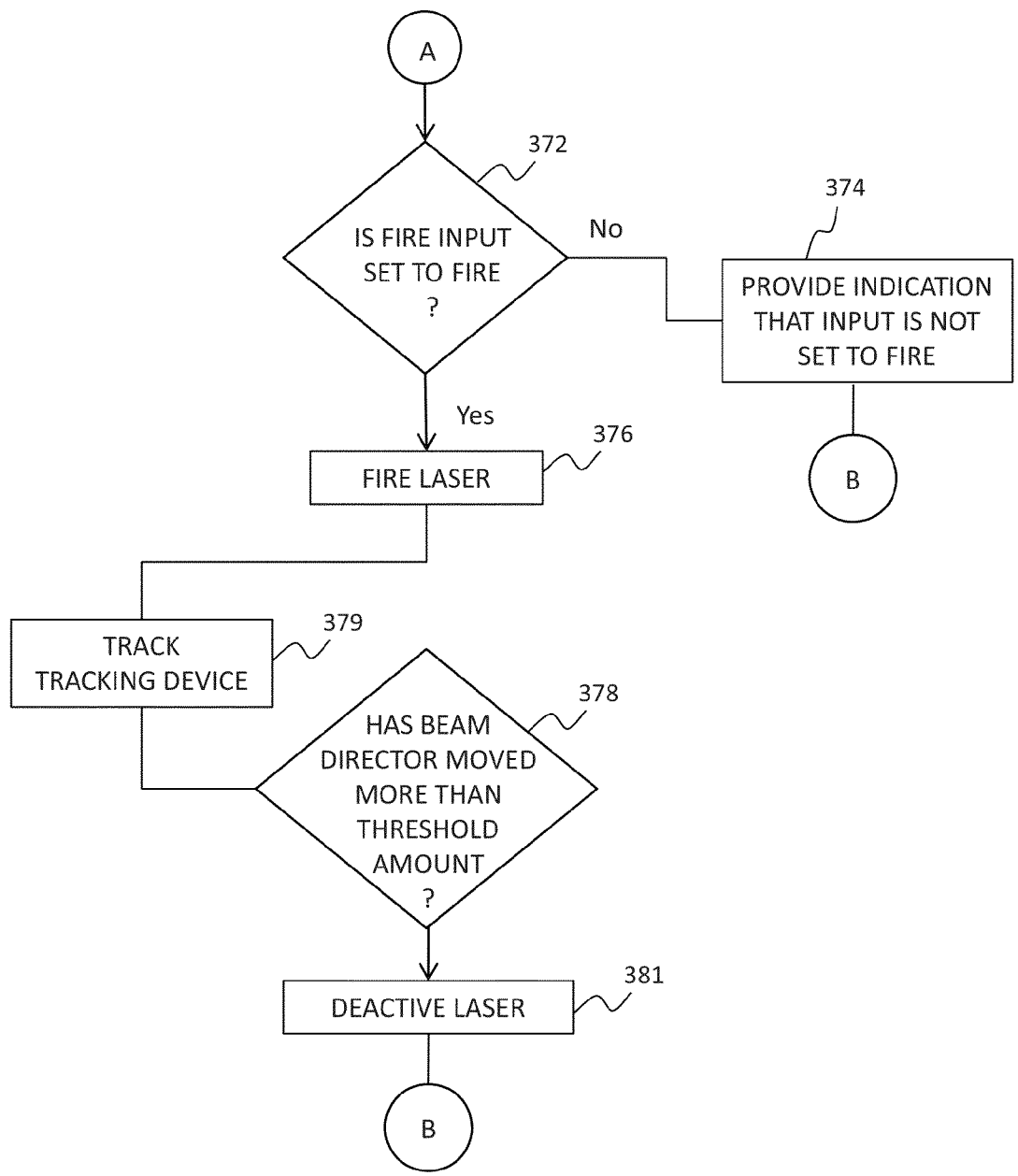

Referring to FIGS. 10A and 10B, an operation of modulation device 100 is illustrated. Referring to FIG. 10A, a check is made by a controller 132 of asset 102 whether warning/cuing system 130 is active, as represented by block 360. Further, warning/cuing system 130 is set to survey mode, as represented by block 362. In survey mode, warning/cuing system 130 monitors the environment around asset 102 to determine if a mobile tracking device 110 is approaching asset 102, as represented by block 364. If a mobile tracking device 110 is detected by warning/cuing system 130, then the controller 132 of asset 102 determines the coordinates of mobile tracking device 110, as represented by block 366. Warning/cuing system 130 may also sound an alarm or provide another indication of mobile tracking device 110 to the operator of asset 102. Exemplary coordinates for the case when the asset is airplane 102 are the azimuth and elevation angles of mobile tracking device 110 relative to airplane 102.

The controller 132 of asset 102 passes the coordinates of mobile tracking device 110 to modulation device 100, as represented by block 368. Modulation device 100 moves rotatable head 184 to the specified angular position and FLIR system 212 is directed at the specified coordinates. FLIR system 212 may be gimbaled to move independently within housing 180. The controller 132 of asset 102 determines if mobile tracking device 110 has acquired mobile tracking device 110 with tracking module 210, as represented by block 370. If modulation device 100 has not acquired mobile tracking device 110, new coordinates of mobile tracking device 110 are determined and passed again to modulation device 100. As such, modulation device 100 remains slaved to controller 132. If modulation device 100 has acquired mobile tracking device 110 then the initial coordinates corresponding to the lock on location of mobile tracking device 110 are saved by system controller 154, as represented by block 371.

Next, system controller 154 of modulation device 100 checks to see if modulation device 100 is authorized to fire continuous wave laser 166, as represented by block 372. Continuous wave laser 166 is authorized to fire when fire input 145 is set to fire. If continuous wave laser 166 is not authorized to fire, then an indication of this is provided to the operator of modulation device 100, as represented by block 374. Exemplary indications include visual alarms, audio alarms, tactile alarms, and combinations thereof. If continuous wave laser 166 is authorized to fire, then continuous wave laser 166 is fired at mobile tracking device 110. Beam control module 162 has already adjusted the output direction of collimated beam 176 to coincide with the direction to modulation device 100.

After modulation device 100 has acquired mobile tracking device 110, beam pointing system 210 tracks the location of mobile tracking device 110 and updates the coordinates for mobile tracking device 110, as represented by block 379. Beam control module 162 rotates and reflector 179 tilts, as necessary, to maintain collimated beam 176 on mobile tracking device 110.

The position of beam control module 162 is monitored to determine when it has moved a threshold amount, as represented by block 378. Once mobile tracking device 110 has changed direction by a threshold amount, it no longer is locked on asset 102 and the threat to asset 102 is neutralized. This change in direction of mobile tracking device 110 is indicated by the change in direction of beam control module 162 to keep collimated beam 176 on mobile tracking device 110. Once the threshold amount is reached, continuous wave laser 166 is deactivated as represented by block 381. Control is again passed back to warning/cuing system 130 to monitor for additional mobile tracking devices 110.

In one embodiment, the threshold amount is about 10 degrees in either the azimuth or elevation directions. In one embodiment, the threshold amount is about 5 degrees in either the azimuth or elevation directions. In one embodiment, the threshold amount is about 3 degrees in either the azimuth or elevation directions. In one embodiment, system controller 154 monitors the time since mobile tracking device 110 was acquired by modulation device 100 and deactivates continuous wave laser 166 once a threshold amount of time has passed.

In one embodiment, beam pointing system 210 has a narrower field of view than sensor modules 131 of warning/cuing system 130. As such, sensor modules 131 are able to survey the surrounding environment for mobile tracking device 110 approaching from various directions, while beam pointing system 210 is fixed on the narrow portion of the environment surrounding a detected mobile tracking device 110.

In one embodiment, warning/cuing system 130 is integrated into modulation device 100 and system controller 154 detects the launch of a mobile tracking device 110 based on the images captured by warning/cuing system 130. Although various tasks are discussed as being carried out by one of warning/cuing system 130, controller 132, and system controller 154, these may be carried out by a common controller.

As mentioned herein output beam 176 is produced by a continuous wave laser 166. Output beam 176 is able to defeat mobile tracking devices 110 which modulate the incoming electromagnetic radiation even though output beam 176 is not pulsed and contains no mobile tracking device specific codes. Output beam 176 is also effective against imaging detection systems of more advanced mobile tracking device 110. Exemplary mobile tracking device specific codes include jamming codes.

Figure 11:
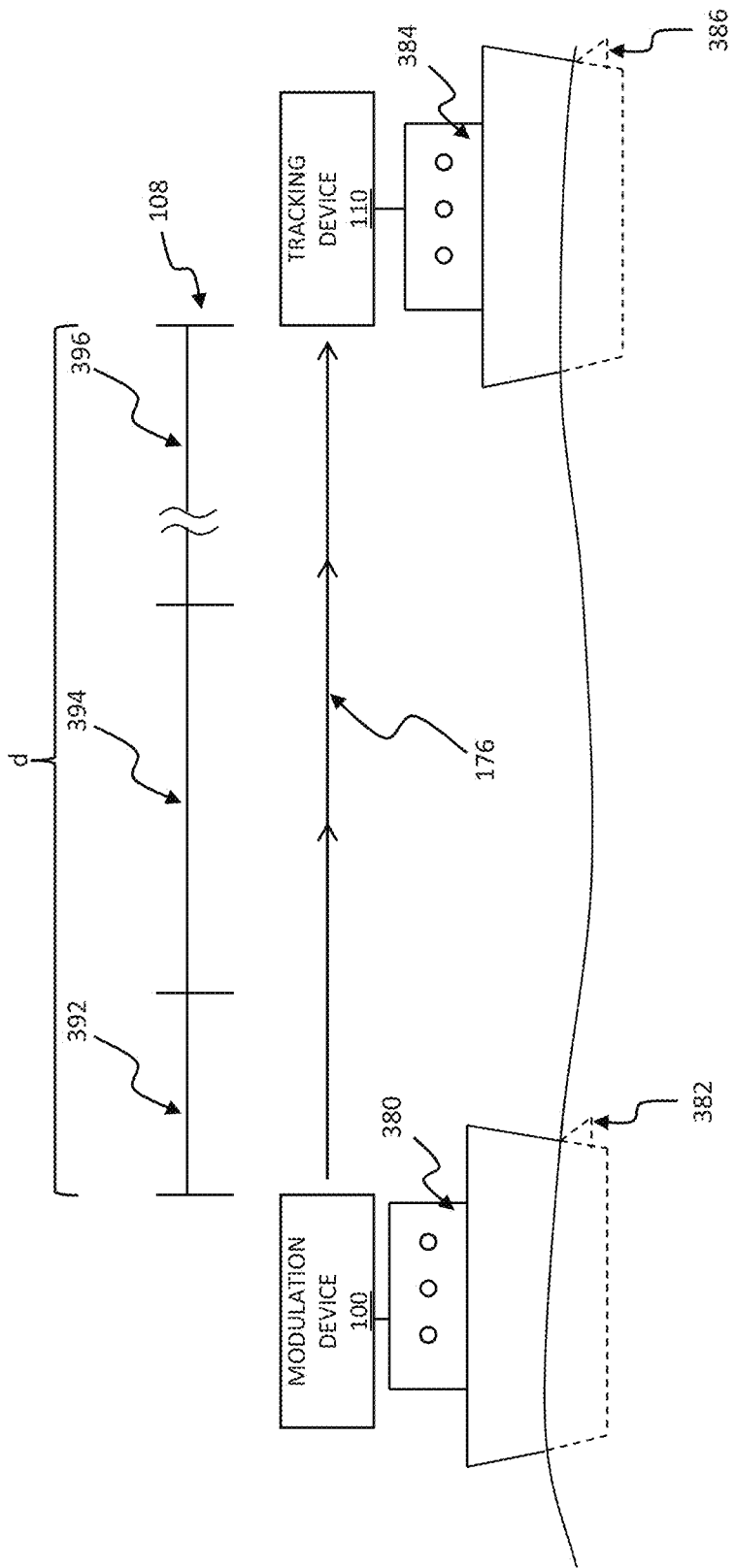
FIG. 11 illustrates a representative asset being tracked by a representative mobile tracking device.

Referring to FIG. 11, a ship 380 is shown having a rudder 382 and modulation device 100. Also shown is a second ship 384 having a rudder 386 which directs the direction of travel of second ship 384. Second ship 384 also incorporates a mobile tracking device 110. Second ship 384 is attempting to track first ship 380 and close the distance between first ship 380 and second ship 384. Mobile tracking device 110 generates course correction signals for second ship 384 so that second ship 384 continues to close on first ship 380. In this example, mobile tracking device 110 does not include a separate propulsion system 112 and guidance system 114. Rather, second ship 384 has its own propulsion system, such as an engine, and rudder 386 directs the travel path of second ship 384 based on input from controller 116.

As illustrated in FIG. 3, telescope 120 of mobile tracking device 110 attempts to collect a large amount of electromagnet radiation to extend the viewing range of the modulation device 100. The distance d indicated in FIG. 11, corresponds to a viewing distance of mobile tracking device 110 which is the distance at which mobile tracking device 110 is first able to detect first ship 380. At distances beyond distance d, mobile tracking device 110 is not able to see first ship 380. Of course, mobile tracking device 110 may be closer to first ship 380 than the distance d and in fact over time mobile tracking device 110 tracks first ship 380 so that second ship 384 closes the distance between second ship 384 and first ship 380.

Modulation device 100, upon locking on the position of mobile tracking device 110, fires continuous wave laser 166 such that output beam 176 is received by telescope 120 of mobile tracking device 110. Output beam 176 has different effects on mobile tracking device 110 depending on the separation of mobile tracking device 110 from modulation device 100. Distance d is illustratively divided into three bands, a near distance band 392, a mid distance band 394, and a far distance band 396. At distances in near distance band 392, the energy of output beam 176 explodes seeker head 115 and destroys mobile tracking device 110. At distances in mid distance band 394, the energy of output beam 176 destroys the functionality of detector 118. In one example, a modulation device 100 including a 3 kW Ytterbium continuous fiber laser as continuous wave laser 166 destroyed a focal plane array detector of a mobile tracking device 110 at a distance of about 3 kilometers.

At distances in far distance band 396, the energy of output beam 176 produces a plurality of internal localized sources within mobile tracking device 110. These internal localized sources are produced by the energy of output beam 176 being absorbed by the optical components of mobile tracking device 110 which then reradiate the absorbed energy in multiple wavelengths, similar to a blackbody source. Referring to FIG. 3, six internal localized sources 400 are illustrated. Sources 400A and 400B correspond to filter 125. Source 400C corresponds to optical window 128. Source 400D corresponds to secondary mirror 123. Source 400E corresponds to primary mirror 121. Source 400F corresponds to optics 124. The sources 400 may be produced based on the absorption characteristics of the material of each component or the presence of an imperfection in a component. For instance, optical window 128 may become scratched during travel resulting in an imperfection that produces source 400C. Although six sources 400 are illustrated, a single source 400 or other number of sources 400 may be produced at various times.

The source 400 produces infrared energy which is brighter than the infrared signature of asset 102 being tracked by mobile tracking device 110. As such, controller 116 of mobile tracking device 110 interprets the respective source 400 as asset 102 instead of asset 102 itself. If source 400 is off-axis, this will cause controller 116 to try to center source 400 resulting in error signal 129 being increased. Guidance system 114 will then turn mobile tracking device 110 in an attempt to center source 400. This results in mobile tracking device 110 turning away from the location of asset 102. Since source 400 is radiating from a portion of mobile tracking device 110, it cannot be centered. Output beam 176 does not require a mobile device specific code to defeat mobile tracking device 110. Therefore, no knowledge of the modulation scheme of mobile tracking device 110 is required to defeat mobile tracking device 110. In one embodiment, the power level of continuous wave laser 166 is about 3 kW exiting modulation device 100.

Source 400 do not explode mobile tracking device 110, such as what happens in near distance band 392, nor is detector 118 of mobile tracking device 110 destroyed, such as what happens in mid distance band 394. Rather, source 400 confuses controller 116 to believe that one or more (if multiple sources) additional objects are present in the field of view of mobile tracking device 110 with a higher intensity than asset 102. Controller 116 tracks the brightest object in its field of view and thus attempts to track one of sources 400, instead of asset 102.

In far distance band 396, mobile tracking device 110 is not destroyed, but rather sent off course. As mobile tracking device 110 approaches modulation device 100 the power level of output beam 176 increases exponentially resulting in detector 118 being destroyed in mid distance band 394 and/or mobile tracking device 110 exploding in near distance band 392. Of course, if mobile tracking device 110 is engaged in far distance band 396 mobile tracking device 110 likely will not enter mid distance band 394 because mobile tracking device 110 will be directed in a different direction due to output beam 176.

Figure 12:
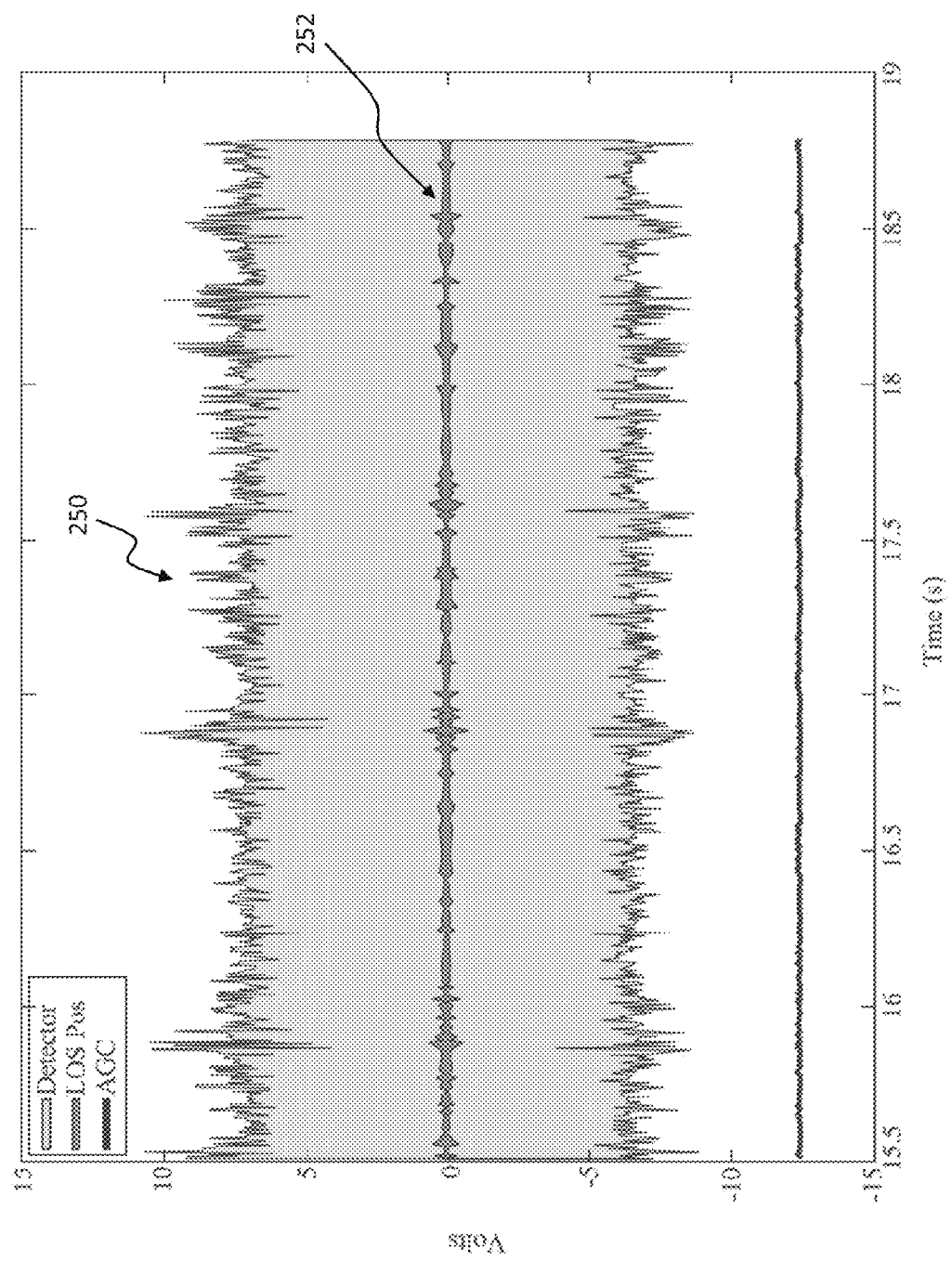
FIGS. 12 and 13 represent the response characteristics of a mobile tracking device following an asset.
Figure 13:
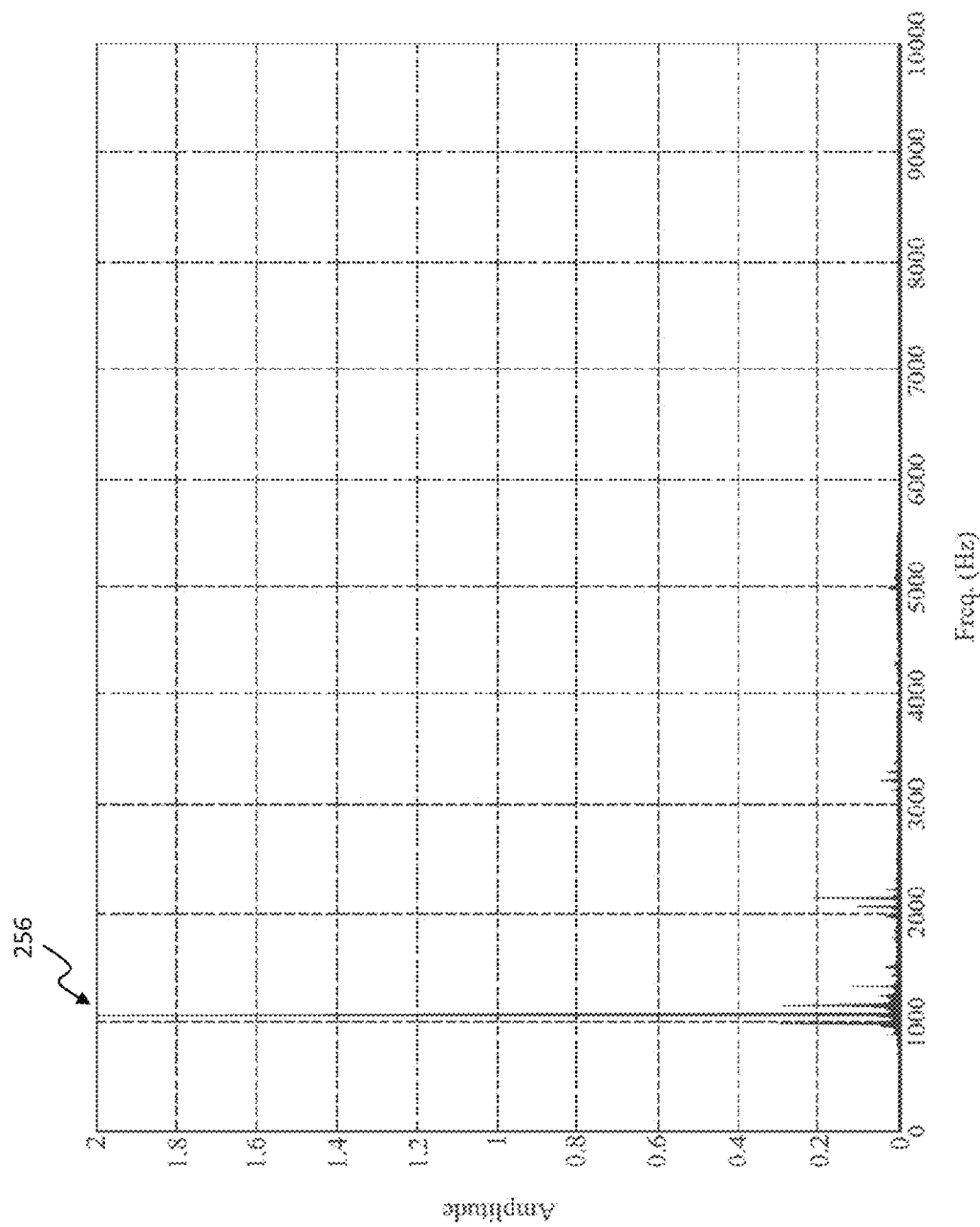
Figure 14:
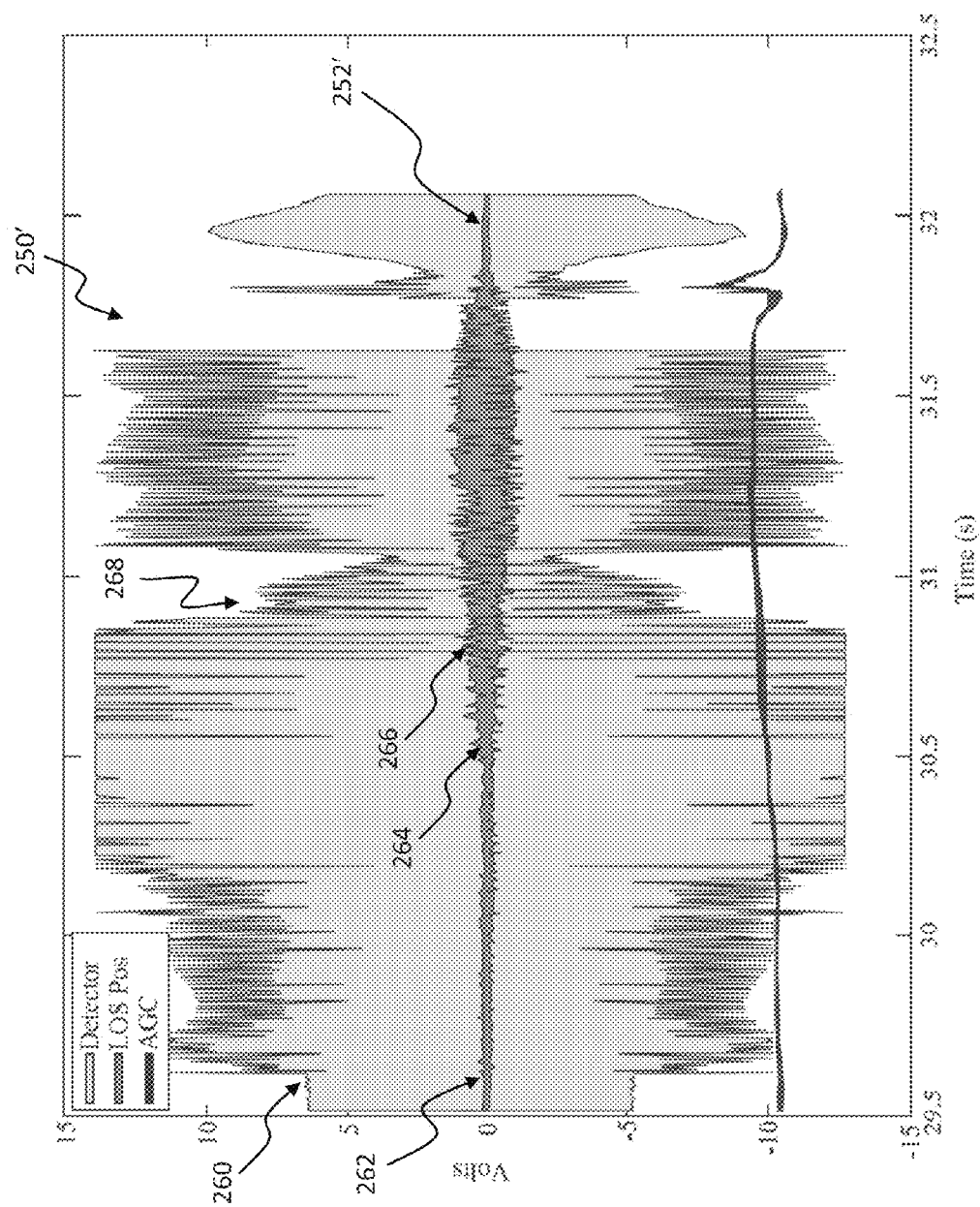
FIGS. 14 and 15 represent the response characteristics of a mobile tracking device following an asset and being subsequently illuminated by a modulation device.
Figure 15:
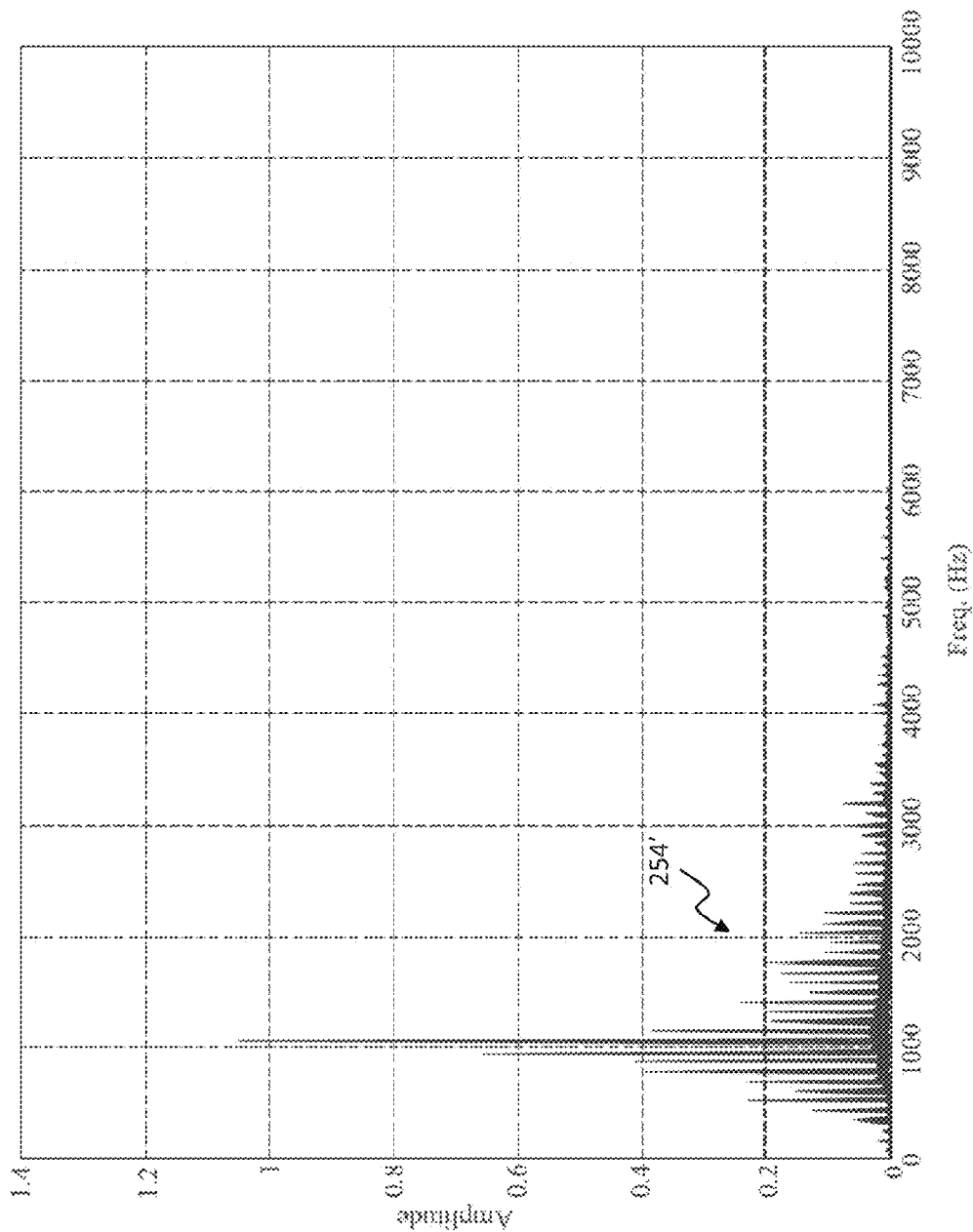

The effects of sources 400 are shown through a comparison of FIGS. 14 and 15 with FIGS. 12 and 13. Referring to FIG. 12, a typical response of a mobile tracking device 110 in far distance band 396 is shown. The degree of turn being carried out by a mobile tracking device 110 is proportional to a voltage associated with a gyroscope of the seeker head 115. In FIG. 12, a raw voltage of detector 118 is shown as curve 250. Also shown is the voltage associated with the gyroscope of the seeker head 115 as curve 252. The amplitude of curve 252 corresponds to error signal 129. The curve 252 shown in FIG. 12, represents a mobile tracking device 110 which has locked onto an asset 102 and is following directly behind the asset 102. The Fourier transform of curve 250 is shown in FIG. 13. As shown in FIG. 13, the spectrum 254 for curve 250 is generally tightly defined around 1000 Hz. This is generally consistent with the modulation scheme of the mobile tracking device 110 when it is inline with asset 102.

Referring to FIG. 14, a 3 kilowatt, continuous wave, infrared, Ytterbium single mode fiber laser with an $m^2$ of 1 was used as continuous wave laser 166 of modulation device 100 associated with an asset 102. In tests, a mobile tracking device 110 was fired at asset 102. Modulation device 100 directed a continuous beam of optical energy 176 at the optical window 128 of mobile tracking device 110. The continuous beam of optical energy causes the generation of sources 400 which are falsely recognized by mobile tracking device 110 as asset 102.

Referring to FIG. 14, the corresponding curves 250' and 252' for the above example are shown. A first portion 260 of curve 250' (and corresponding portion 262 of curve 252') are shown prior to activation of continuous wave laser 166. As shown by portion 262, the travel of mobile tracking device 110 is fairly straight. Continuous wave laser 166 is activated at point 264. This results in detector 118 being flooded with IR energy as represented by the increase in amplitude of curve 250' and the generation of sources 400. The generation of sources 400 appears to be later in time potentially indicating the need for the components of mobile tracking device 110 to heat up to cause sources 400. At portion 264 of curve 252' controller 116 is instructing guidance system 114 to turn mobile tracking device 110 more aggressively. This increase in turning of mobile tracking device 110 increases in portion 266 even as the intensity of curve 250' falls in portion 268. This fall in intensity is indicative of mobile tracking device 110 moving far off course so that not as much of collimated beam 176 enters optical window 128. As shown in FIG. 15, the spectrum 254' for curve 250' is considerably broadened compared to spectrum 254 of FIG. 12.

Figure 2A:
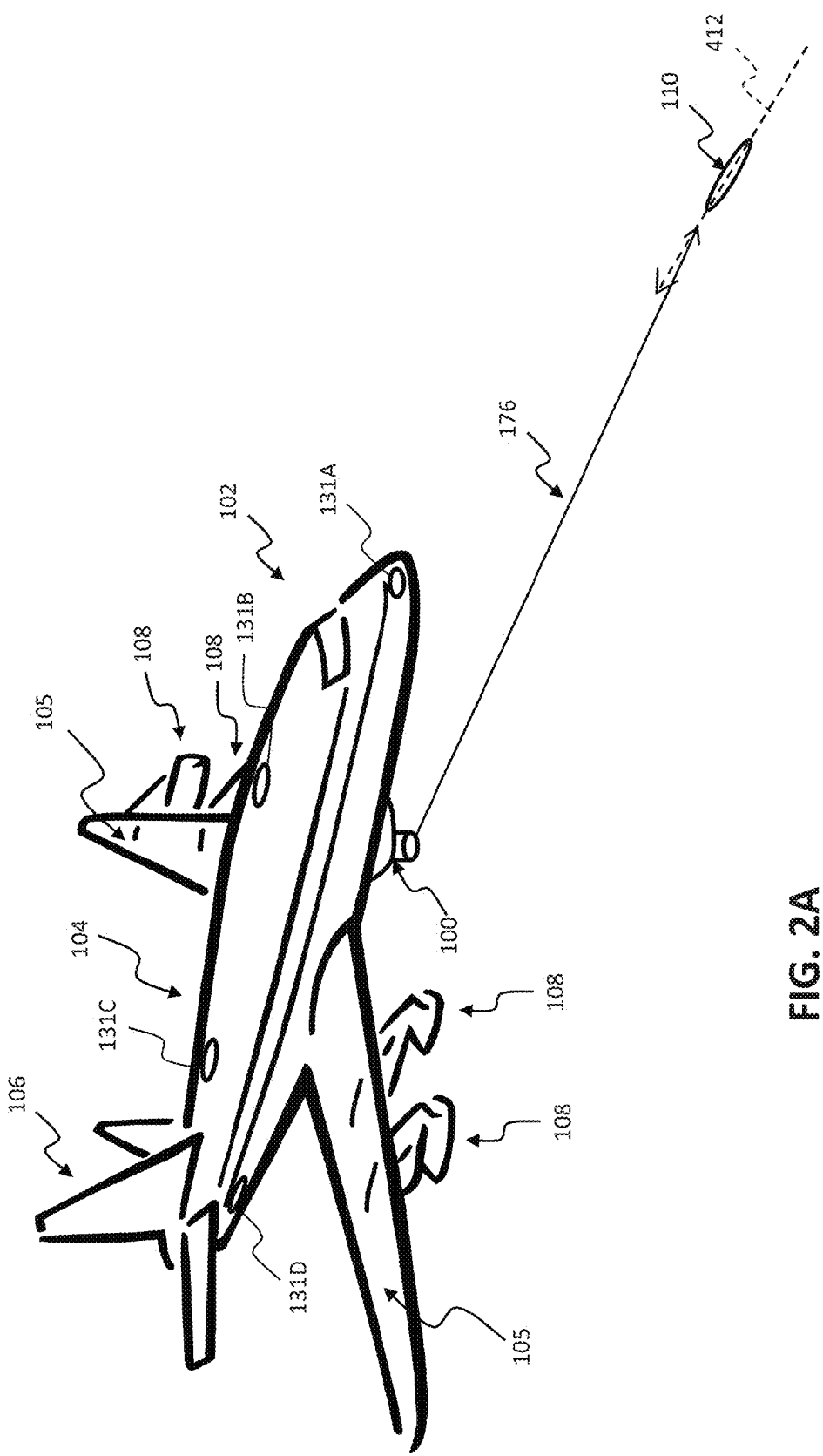
FIG. 2A illustrates the representative asset of FIG. 2 with a mobile tracking device approaching the representative asset along a first direction and optical energy from the modulation device being directed at the mobile tracking device.
Figure 2B:
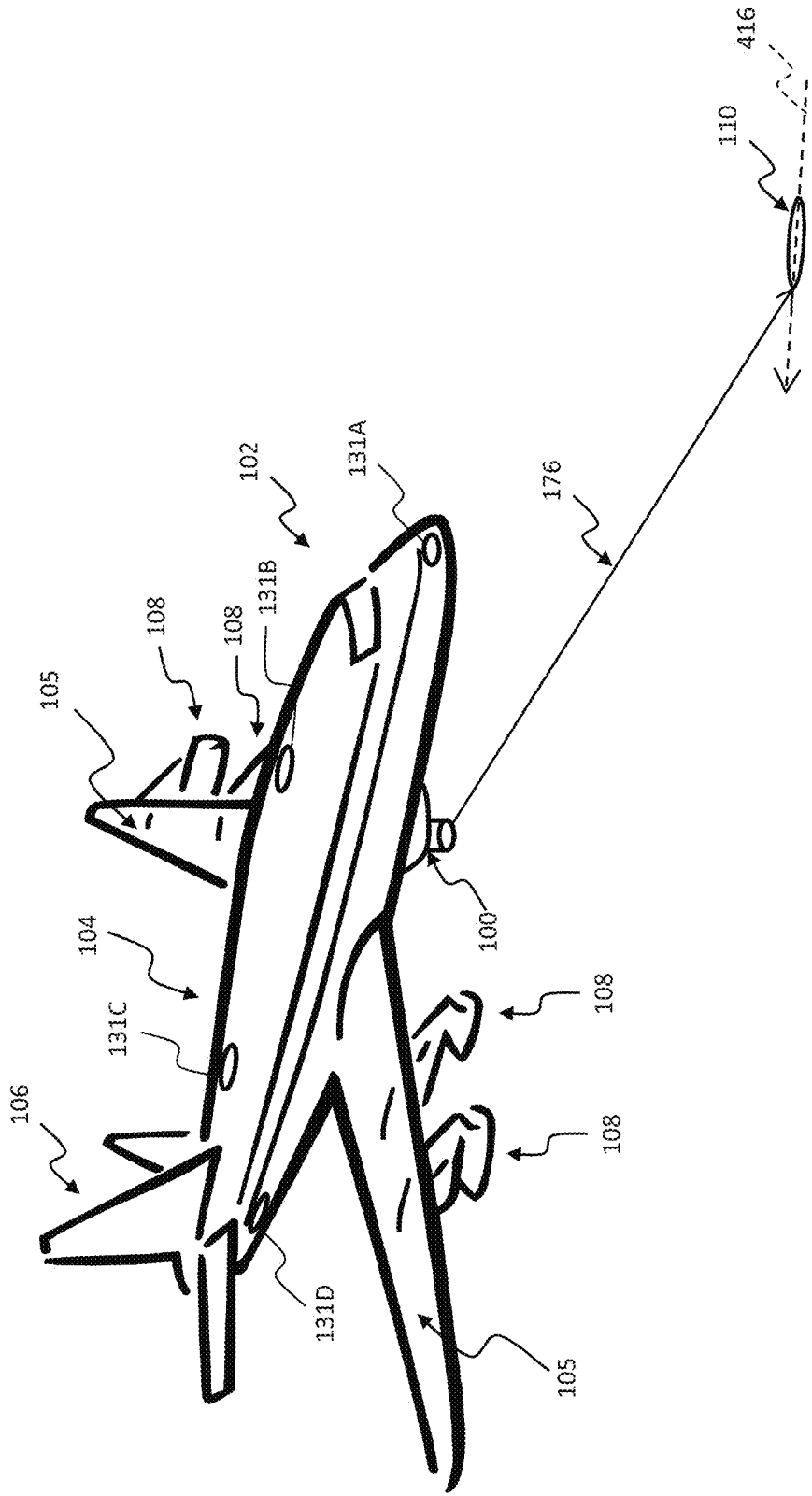
FIG. 2B illustrates the mobile tracking device changing its direction of travel to a second direction due to the optical energy directed from the modulation device at the mobile tracking device.
Figure 2C:
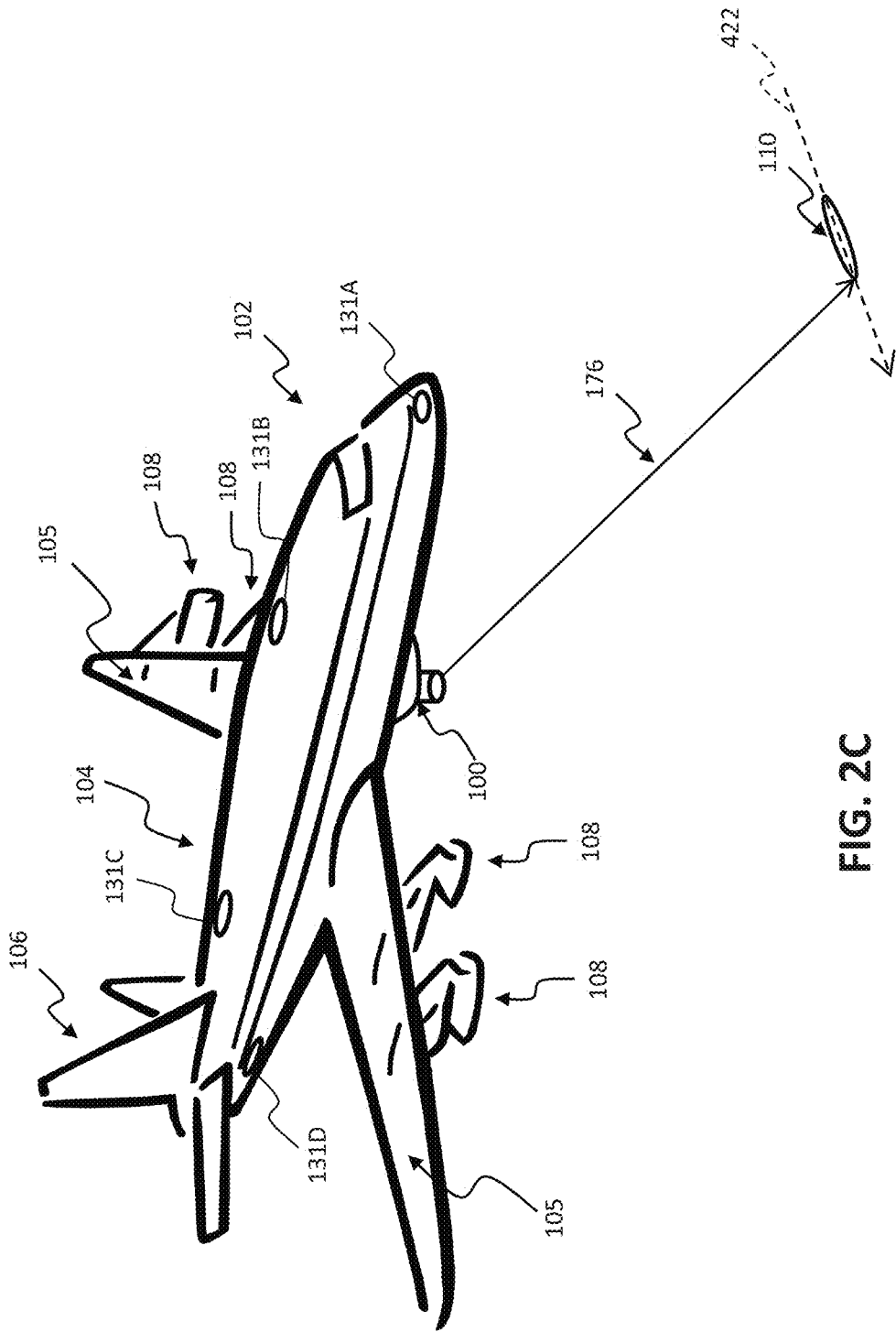
FIG. 2C illustrates the mobile tracking device changing its direction of travel to a third direction due to the optical energy directed from the modulation device at the mobile tracking device.
Figure 2D:
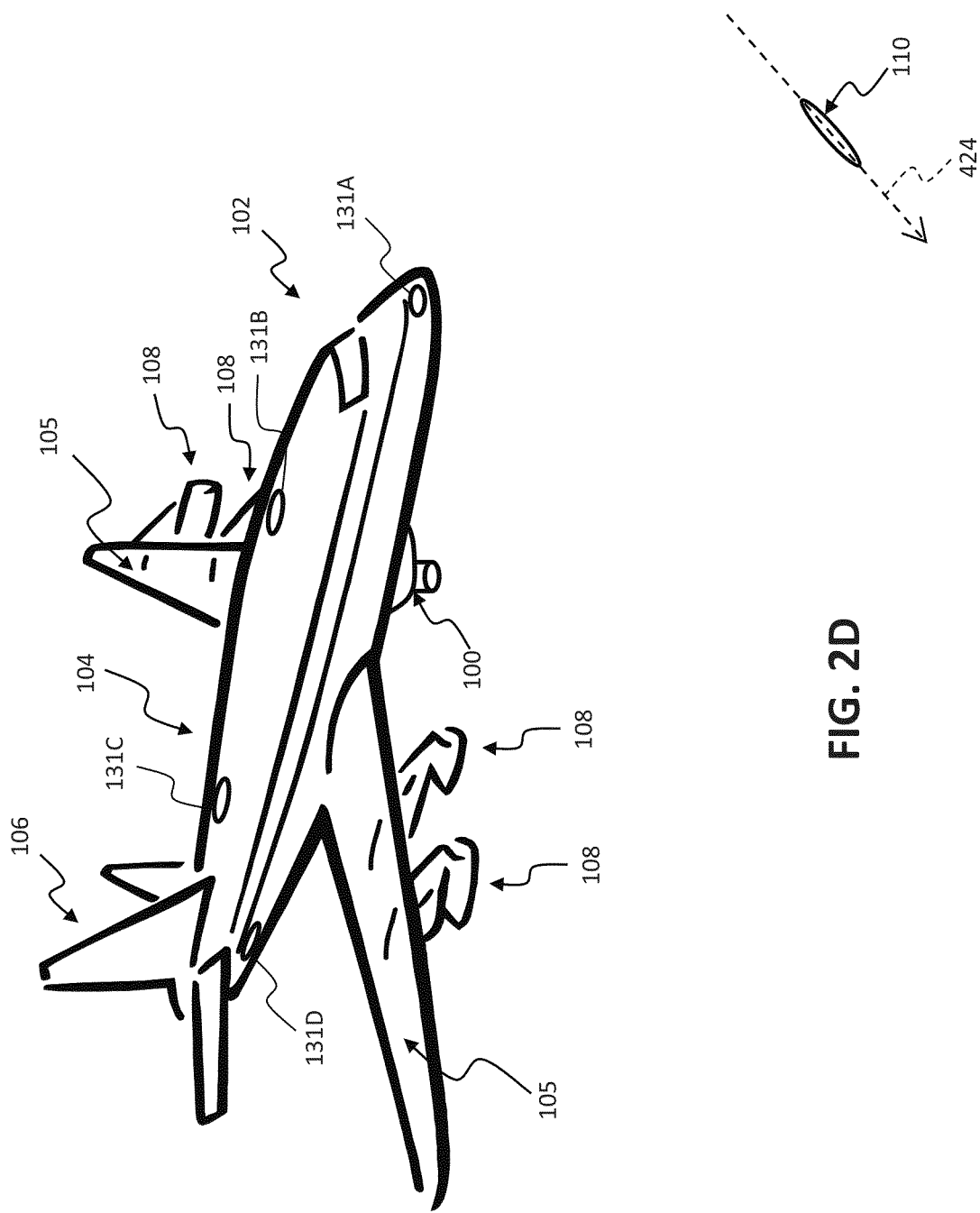
FIG. 2D illustrates the mobile tracking device changing its direction of travel to a fourth direction due to the optical energy directed from the modulation device at the mobile tracking device.
Figure 16:
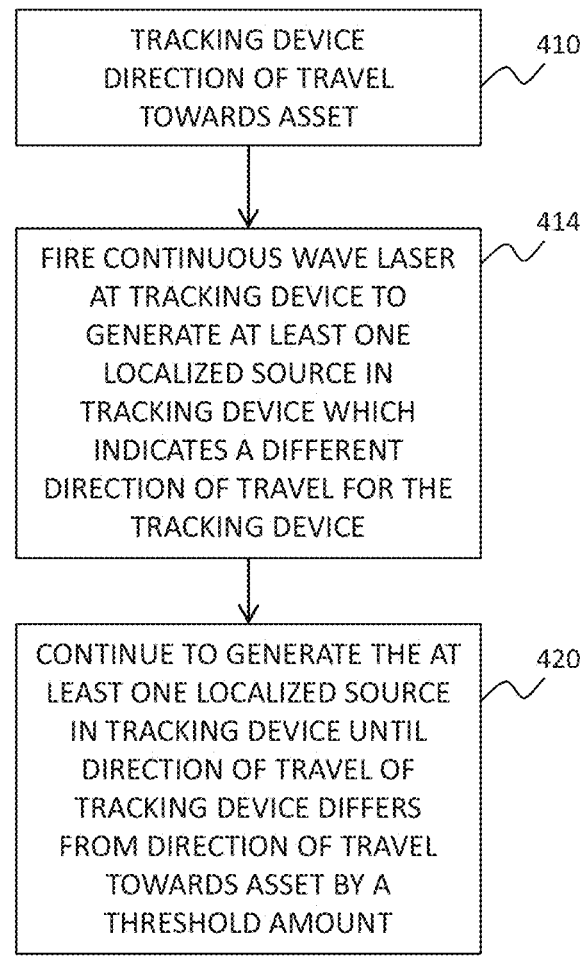
FIG. 16 illustrates a method of countering a mobile tracking device with a modulation device.

Referring to FIG. 16, mobile tracking device 110 is traveling in a direction towards asset 102, as represented by block 410. This is illustrated in FIG. 2A wherein an airborne mobile tracking device 110 is shown traveling in direction 412 towards asset 102. As explained herein, modulation device 100 fires continuous wave laser 166 to direct output beam 176 towards mobile tracking device 110. This causes the generation of at least one localized source 400 within mobile tracking device 110 which is within a field of view of mobile tracking device 110. These one or more localized sources 400 are brighter than the infrared energy radiated from asset 102 and are generated at locations which do not correspond with the current direction 412 of mobile tracking device 110, as represented by block 414 in FIG. 16. As such, controller 116 attempts to point mobile tracking device 110 at the brighter source 400 and in doing so changes the direction of mobile tracking device 110 to direction 416 as shown in FIG. 2B. Beam control module 162 alters the direction of output beam 176 to coincide with the new direction of mobile tracking device 110, as represented by block 420 in FIG. 16. This again causes the generation of the localized sources 400 within mobile tracking device 110 which are within a field of view of mobile tracking device 110. As such, controller 116 attempts to point mobile tracking device 110 at the brighter source 400 and in doing so changes the direction of mobile tracking device 110 to direction 422 as shown in FIG. 2C. Beam control module 162 alters the direction of output beam 176 to coincide with the new direction of mobile tracking device 110. Once again this causes the generation of the localized sources 400 within mobile tracking device 110 which are within a field of view of mobile tracking device 110. As such, controller 116 attempts to point mobile tracking device 110 at the brighter source 400 and in doing so changes the direction of mobile tracking device 110 to direction 424 as shown in FIG. 2D. In moving beam control module 162 to track mobile tracking device 110 along the direction 424, rotatable head 184 exceeds the threshold rotation amount and continuous wave laser 166 is deactivated, as shown in FIG. 2D.

Unlike prior art devices, modulation device 100 is not mobile tracking device 110 specific. Rather, modulation device 100 is effective against both imaging and non-imaging mobile tracking devices 110. Further, modulation device 100 does not require a mobile device specific code to be known in advance. Rather, modulation device 100 relies on the continuous provision of optical energy into mobile tracking device 110 to produce localized sources 400 within the field of view of mobile tracking device 110 such that detector 118 is confused as to the location of asset 102.

In another example of the use of modulation device 100, a 3 kW, continuous wave, infrared, Ytterbium single mode fiber laser was used as continuous wave laser 166 of modulation device 100 associated with an asset 102. In tests, a plurality of different mobile infrared mobile tracking devices 110 were fired at asset 102 while asset 102 was at ground level. Modulation device each time directed output beam 176 at the optical window of the respective mobile tracking device 110. The modulation device 100 was effective against all of the plurality of different mobile tracking device 110 at a range of up to about 1250 meters from modulation device 100. A computer model was made wherein asset 102 was at ground level, a wavelength of continuous wave laser 166 was set to 1.07 μm, and values for additional parameters modulation device 100 and mobile tracking device 110 were set. The computer model provided a predicted range of up to 1290 meters for a plurality of different mobile tracking device 110. This computer model demonstrated good agreement with the experimentally obtained range of up to 1250 meters.

In a further example of the use of modulation device 100, a 3 kilowatt, continuous wave, infrared, Ytterbium single mode fiber laser was used as continuous wave laser 166 of modulation device 100 associated with an asset 102. In tests, a specific mobile tracking device 110 was fired at asset 102 while asset 102 was at ground level. Modulation device 100 directed output beam 176 at the optical window of mobile tracking device 110. The modulation device 100 was effective against the specific mobile tracking device 110 at a range of up to about 2650 meters from modulation device 100. The above-mentioned computer model provided a predicted range of up to 2440 meters for the specific mobile tracking device 110. This demonstrates good agreement with the experimentally obtained range of up to 2650 meters.

Returning to FIG. 9, in one embodiment, beam pointing system 210 further includes a laser designator system 214. Laser designator system 214 includes a pulsed laser which is directed at mobile tracking device 110 and reflected therefrom. Based on the reflected signal, laser designator system 214 is able to determine a distance from modulation device 100 to mobile tracking device 110. In the case wherein modulation device 100 includes focusing optics 177 or wherein beam expander 172 may be focused, one of system controller 154 and beam pointing system 210 adjusts a focal length of focusing optics 177 to focus output beam 176 at the location of mobile tracking device 110. In one embodiment, output beam 176 is focused at a distance shorter than the determined range to mobile tracking device 110, the distance being chosen based on an estimated speed of mobile tracking device 110. In one embodiment, this distance corresponds to the expected position of mobile tracking device 110 based on assumptions regarding the relative difference in speed between asset 102 and mobile tracking device 110. In one embodiment, the estimated speed of mobile tracking device 110 is selected based on the type of mobile tracking device 110 which is identified based on a retro-reflection received from mobile tracking device 110.

Laser designator system 214, illustratively, has a separate optical window 215 through which the laser beam of laser designator system 214 is sent out of modulation device 100 and the reflection from mobile tracking device 110 is received to determine the distance to mobile tracking device 110. In one embodiment, laser designator system 214 uses the same optical window 190 as output beam 176 and is bore sighted to output beam 176.

Figure 28:
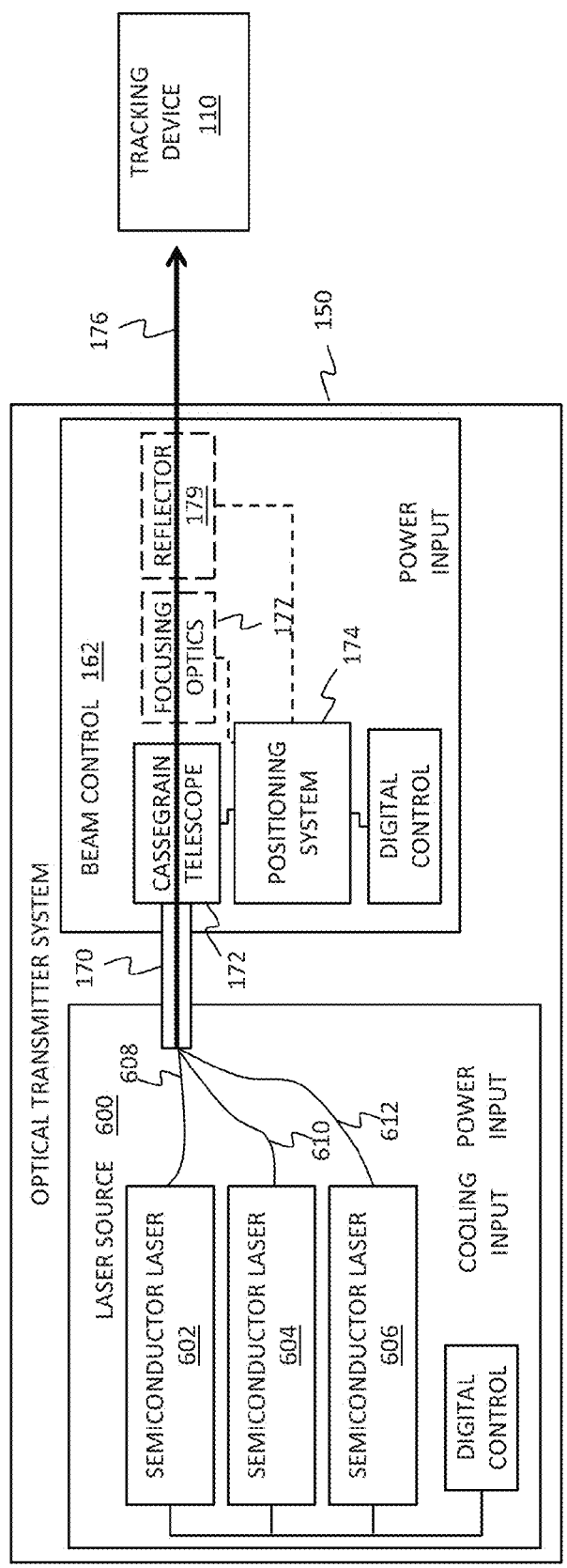
FIG. 28 illustrates a representative view of a modulation device and associated asset.

Referring to FIG. 28, in one embodiment, the optical transmitter system 150 of modulation device 100 includes a laser source 600. Laser source 600 includes a plurality of semiconductor lasers 602-606 which produce optical energy for modulation device 100. In one embodiment, the semiconductor lasers are continuous wave lasers. In one embodiment, lasers 602-606 are quantum cascade lasers. Exemplary quantum cascade lasers include External Cavity Quantum Cascade Lasers available from Daylight Solutions located at 13029 Danielson Street, Suite 130 in Poway, Calif. and Pranalytica located at 1101 Colorado Avenue in Santa Monica, Calif. In one embodiment, the semiconductor lasers have a wavelength of at least about 1 um. In one embodiment, the semiconductor lasers have a wavelength of at least about 2 um.

The output optical energy of each of lasers 602-606 is carried through respective optical conduits 608-612 to beam control module 162. The end of the respective optical conduits 608-612 are positioned generally at a focus of beam expander 172. Beam control unit 162 sends the optical energy produced by each of lasers 602-606 towards mobile tracking device 110. The optical energy of lasers 602-606 is generally incoherently combined to produce a beam with a power level sufficient to function in the same manner as continuous wave laser 166.

In one embodiment, lasers 602-606 combine to produce about 3 kW of power. In one embodiment, the power level of the combined lasers 602-606 is about 5 kW. In one embodiment, the power level of the combined lasers 602-606 is about 10 kW. In one embodiment, the power level of the combined lasers 602-606 is about 20 kW. In one embodiment, the power level of the combined lasers 602-606 is about 50 kW. In one embodiment, the power level of the combined lasers 602-606 is between about 3 kW and 20 kW. In one embodiment, the power level of the combined lasers 602-606 is at least 3 kW. In one embodiment, the power level of the combined lasers 602-606 is at least 3 kW for a duration of at least about 11 minutes. The combined lasers 602-606 may be used together to form the output beam of modulation device 100. In one embodiment, the output beam of modulation device 100 is at least about 60 kW. In one embodiment, the output beam of modulation device 100 is in the range of about 60 kW to about 100 kW.

By using multiple semiconductor lasers, as opposed to a single high power laser, the amount of heat management needed is greatly reduced because the individual semiconductor lasers collectively do not generate the same amount of heat as the high power laser 166.

Figure 17:
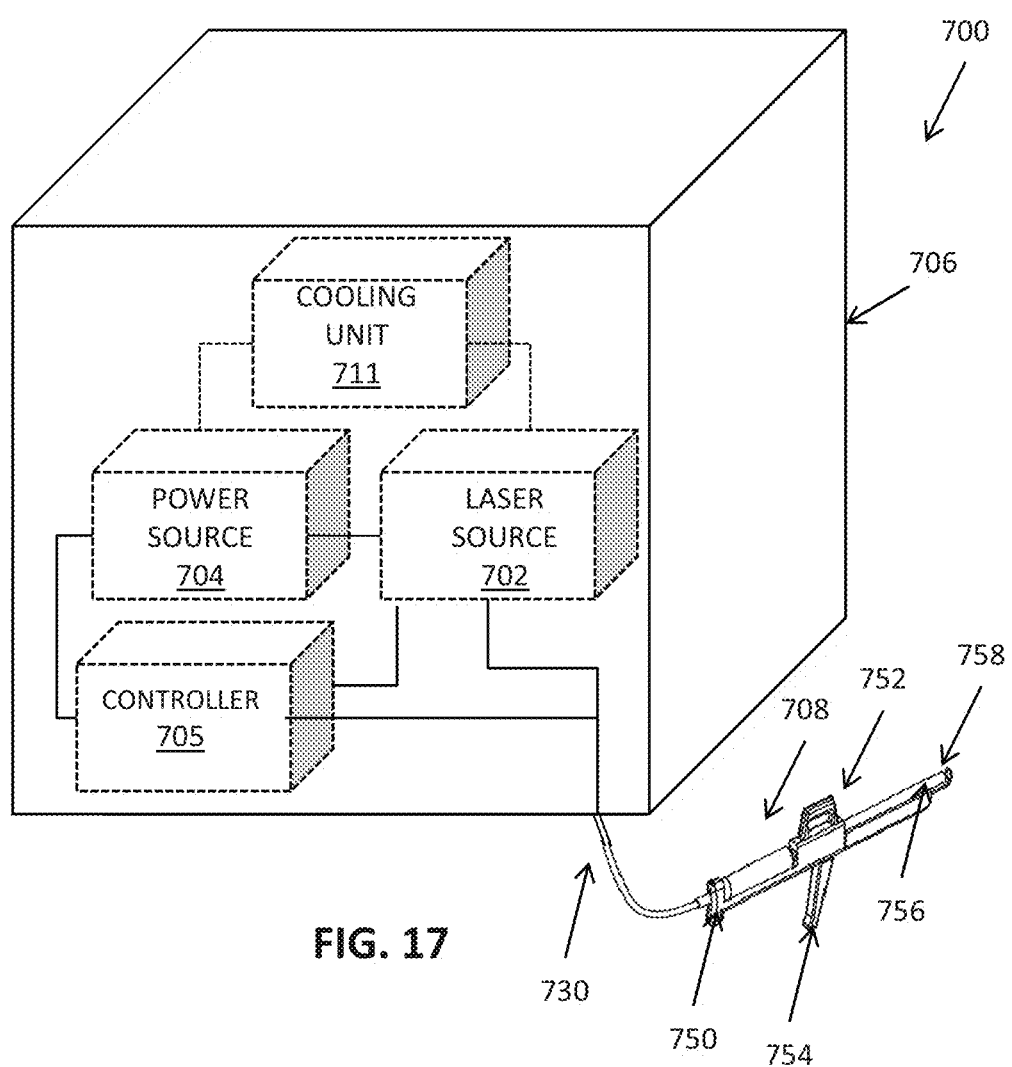
FIG. 17 is a representative view of a portable cutting device.

Referring to FIG. 17, a portable cutting device 700 is shown. The portable cutting device 700 includes a laser source 702, a power supply 704, a storage container 706, and a laser directing device 708. Portable cutting device 700 may be used in multiple applications for cutting through materials. Exemplary materials include wood, masonry, metal, and other materials. Portable cutting device 700 does not require an internal combustion generator and therefore does not have the associated noise and exhaust issues.

A cooling unit 711 may optionally be provided to actively cool one or both of laser source 702 and power supply 704. In one embodiment, cooling unit 711 is an air-cooled chiller. In one embodiment, cooling unit 711 is a thermo-electric cooling system. In one embodiment, cooling unit 711 is an on-demand cooler which directs cooling air at the optical coupler which couples laser source 702 to optical conduit 730. The on-demand cooler may be manually activated or activated based on a monitored temperature sensor value. The cooling air of the on-demand cooler is a non-flammable gas.

Figure 18:
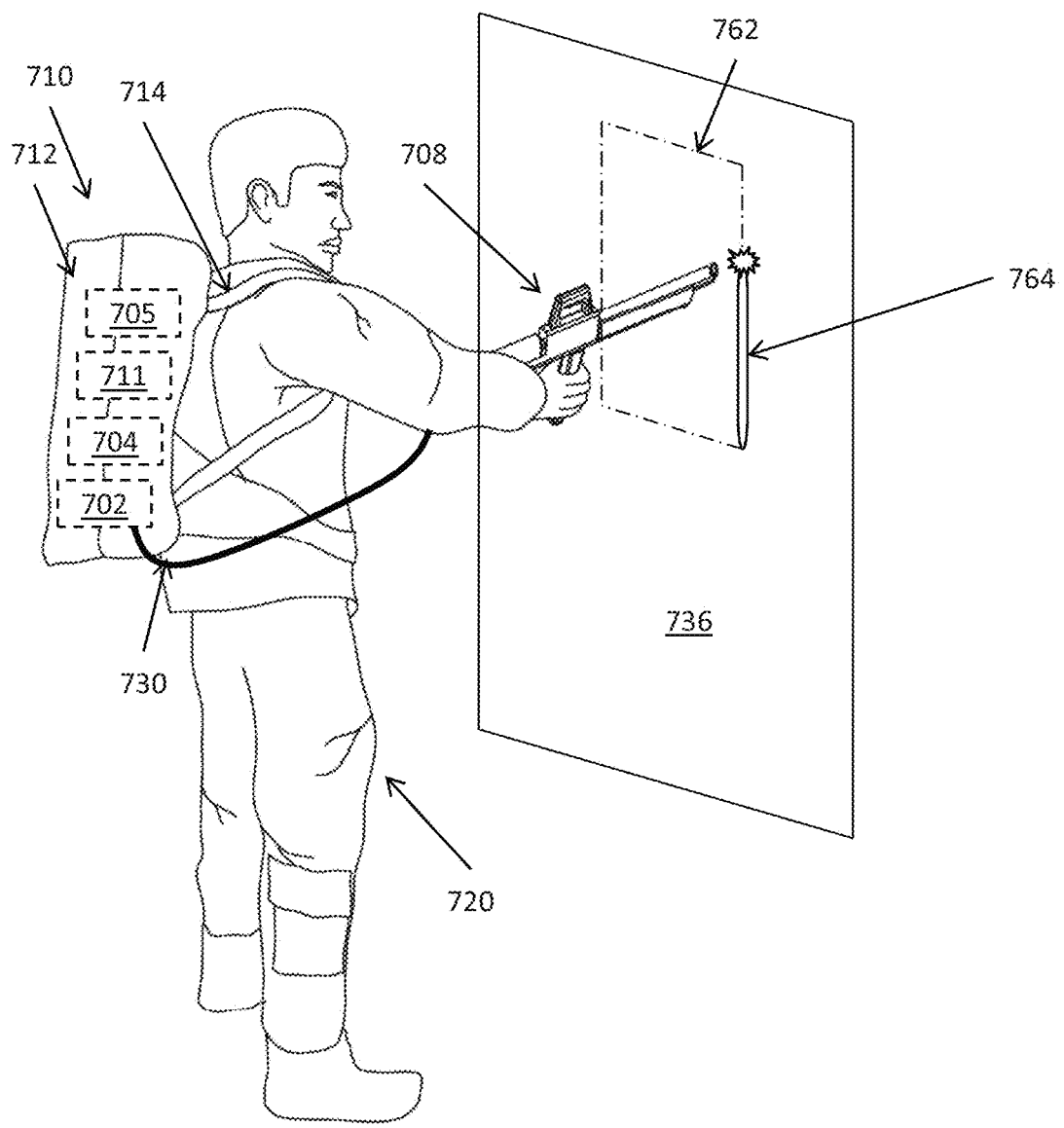
FIG. 18 shows the portable cutting device of FIG. 17 being used to breach a barrier.

In one embodiment, storage container 706 is a backpack, such as backpack 710 shown in FIG. 18. Backpack 710 is worn by a human operator 720. Backpack 710 includes a cargo carrying portion 712 and two straps 714 which are positioned over the shoulders of the human operator 720 and extend under the arms of the human operator 720. Backpack 710 is positioned on the back side of the human operator 720. In one embodiment, storage container 706 is positioned on a front side of the human operator 720. In one embodiment, storage container 706 is positioned to either a left side or a right side of the human operator 720. In one embodiment, storage container 706 is positioned on at least two of a back side, a left side, a front side, and a right side of the human operator 720.

Figure 18A:
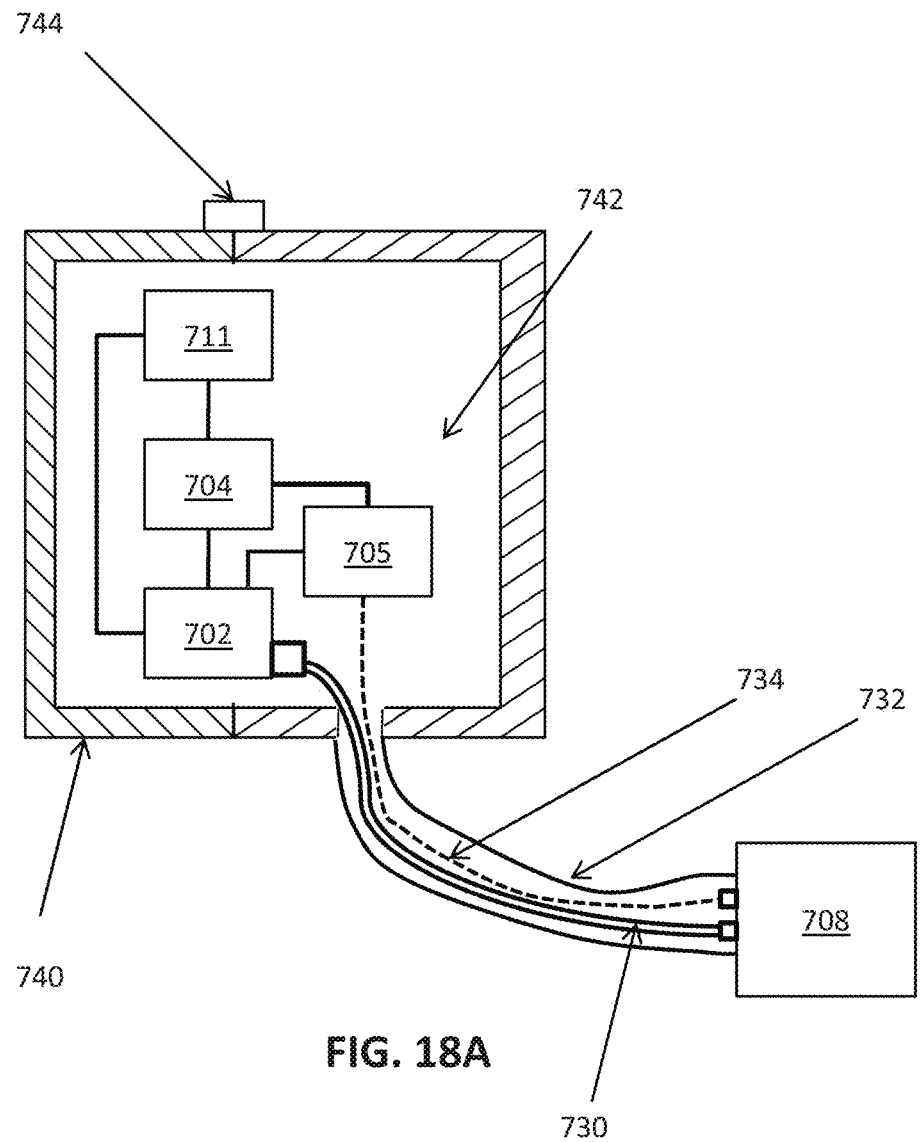
FIG. 18A is a representative view of the cargo carrying portion of the backpack shown in FIG. 18.

In one embodiment, laser source 702, power supply 704, and controller 705 are positioned within cargo carrying portion 712 of backpack 710 for transport by human operator 720. Referring to FIG. 18A, cargo carrying portion 712 is represented. Cargo carrying portion 712 includes a first portion 740 and a second portion 742 which cooperate to form an interior space of cargo carrying portion 712. In one embodiment, cargo carrying portion 712 is made of a flexible material and first portion 740 and second portion 742 are secured together with one or more suitable fasteners 744. Exemplary fasteners include zippers, snaps, and other suitable fasteners. In one embodiment, first portion 740 and second portion 742 are integrally formed and are separatable only along a portion, such as the left side, top side, and right side. In one embodiment, cargo carrying portion 712 is a hard case and first portion 740 and second portion 742 are secured together with one or more suitable fasteners 744. Exemplary fasteners include latches and other suitable fasteners. Regardless of the configuration, first portion 740 and second portion 742 cooperate to provide a closed space for carrying laser source 702, power supply 704, controller 705, and, optionally, cooling unit 711 during transport and the ability to open at least a portion of cargo carrying portion 712 to access laser source 702, power supply 704, controller 705, or cooling unit 711, such as to replace the batteries of power supply 704.

Laser directing device 708 is held by the human operator 720. Laser directing device 708 includes a stock portion 750 which may be positioned next to the shoulder of human operator 720. Laser directing device 708 also includes a handle 752 whereby the hand of the operator may carry laser directing device 708 and a grip 754 which human operator 720 may grasp during operation of portable cutting device 700.

Laser directing device 708 is coupled to laser source 702 through an optical conduit 730. Exemplary optical conduits include fiber optic cable. Laser directing device 708 also includes an optical conduit 756 which is coupled to optical conduit 730. Optical energy generated by laser source 702 travels through optical conduit 730 and optical conduit 756 and is discharged through an end 758 of laser directing device 708 towards a barrier 736 (see FIG. 18). The energy discharged by laser directing device 708 is of sufficient strength to cut the material of barrier 736. Laser directing device 708 includes an optical system 810 which shapes the energy exiting optical conduit 756 of laser directing device 708 to focus it at a focus 814. Focusing optics 760 concentrate the energy onto a defined location on the barrier 736.

Returning to FIG. 18A, optical conduit 730 is coupled to laser source 702 at a location in the interior of cargo carrying portion 712. Optical conduit 730 extends through a wall of cargo carrying portion 712 and is coupled to laser directing device 708 outside of storage container 706 at optical connector 806 (see FIG. 21). In one embodiment, optical conduit 730 couples to laser directing device 708 through grip 754.

Optical conduit 730 is provided in a protective sheath 732. The protective sheath 732 should have a high thermal conductivity and limit a bend radius of optical conduit 730. In one embodiment, protective sheath 732 is made of segmented pieces of metal coupled together. Also included with protective sheath 732 is an electrical control and signal cable 734 which couples controller 705 with components of laser directing device 708. In one embodiment, controller 705 is coupled to a controller 830 of laser directing device 708. In one embodiment, controller 705 is coupled to controller 830 over through a standard RS-232 or RS-422 interface. In one embodiment, signal cable 734 is an optical fiber and controller 705 communicates with controller 830 via any type of standard protocol, such as Internet protocol. As explained herein, controller 830 interfaces with the operator 720, the components of laser directing device 708, and monitors sensors associated with laser directing device 708. Controller 830 then communicates this information to controller 705 which controls the operation of laser source 702.

Laser source 702, in one embodiment, is a continuous wave laser. In one embodiment, laser source 702 is a fiber laser. In one embodiment, laser source 702 is a continuous wave Ytterbium single mode fiber laser. Exemplary continuous wave single mode fiber lasers are provided by IPG Laser GmBH located at 50 Old Webster Road in Oxford, Mass. 01540. Details regarding an exemplary laser source 702 are provided in U.S. patent application Ser. No. 11/973,437, titled POWERFUL FIBER LASER SYSTEM, assigned to IPG Photonics Corporation, the disclosure of which is expressly incorporated by reference herein. Details regarding an exemplary laser source 702 are provided in U.S. patent application Ser. No. 11/611,247, titled FIBER LASER WITH LARGE MODE AREA FIBER, assigned to IPG Photonics Corporation, the disclosure of which is expressly incorporated by reference herein. In one embodiment, laser source 702 is a solid state laser.

Figure 27:
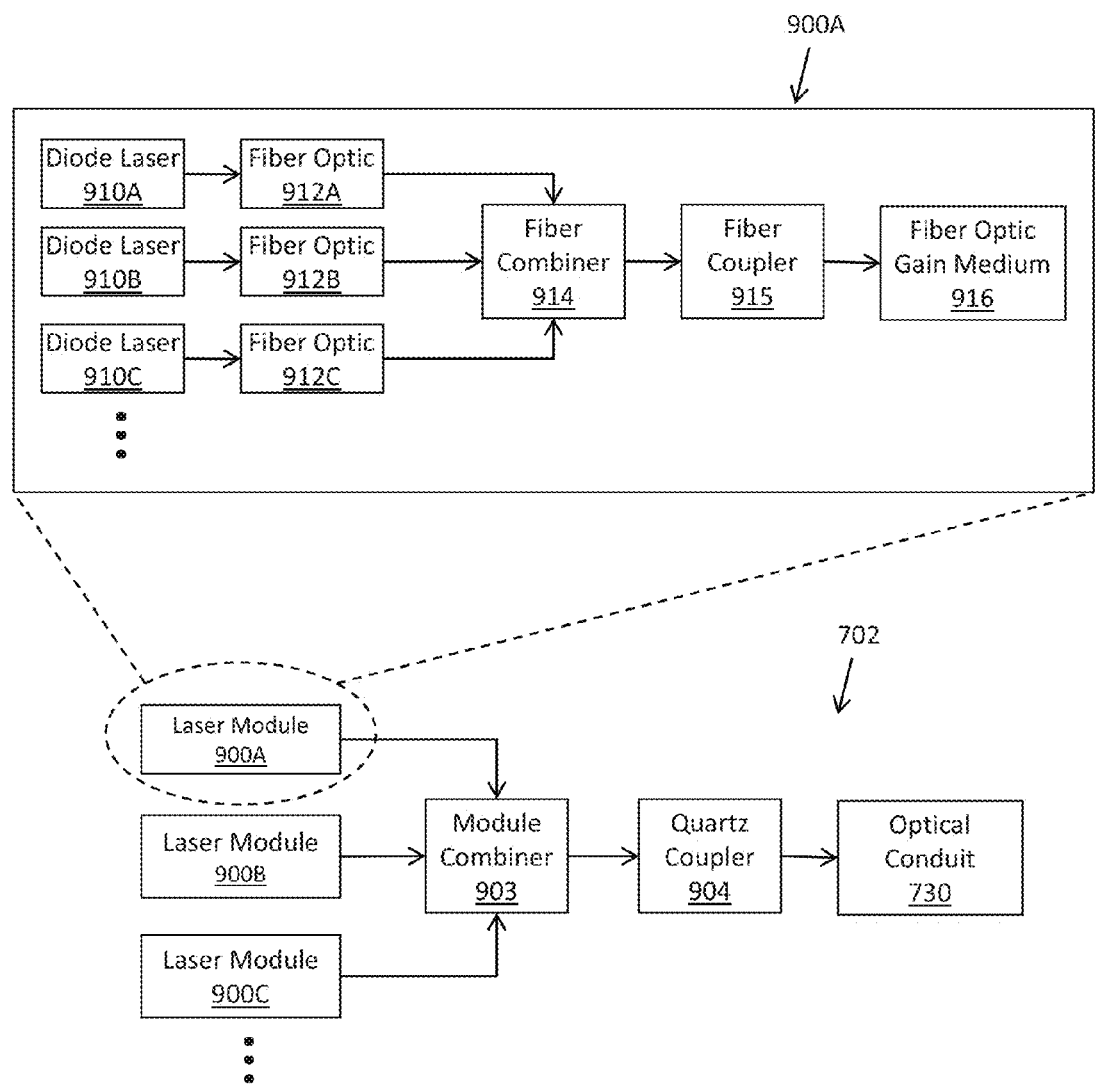
FIG. 27 illustrates an exemplary laser source.

Referring to FIG. 27, an exemplary configuration of laser source 702 is shown. Laser source 702 includes a plurality of individual modules 900 each of which provide a single mode 1.07 micrometer output beam. The output of each of modules 900 is combined together through a module combiner 903 which brings the energy together in a single beam. This combined beam is coupled to optical conduit 730 through a quartz coupler 904. Although three laser modules 900 are illustrated any number of laser modules 900 may be included.

The components of a given laser module 900 are also shown in FIG. 27. The laser module 900 includes a plurality of diode lasers 910 each of which are coupled into a respective Ytterbium fiber 912. The output of the Ytterbium fibers 912 are combined through a fiber combiner 914 which brings the energy together. This energy is fed through a coupler 915 into an Ytterbium fiber optic gain medium 916 which produces there from a single mode 1.07 micrometer output beam. Although three diode laser sets 910 are illustrated any number of diode laser sets 910 may be included.

In one embodiment, the power of laser source 702 is about 3 kilowatts. In one embodiment, the power level of laser source 702 is about 5 kilowatts. In one embodiment, the power level of laser source 702 is about 10 kilowatts. In one embodiment, the power level of laser source 702 is about 20 kilowatts. In one embodiment, the power level of laser source 702 is about 50 kilowatts. In one embodiment, the power level of laser source 702 is between about 3 kilowatts and 20 kilowatts. In one embodiment, the power level of laser source 702 is at least 3 kilowatts.

In one embodiment, power supply 704 is a portable power supply. An exemplary portable power supply is one or more batteries, such as rechargeable batteries. Exemplary rechargeable batteries include lithium-ion batteries and lithium polymer batteries. Exemplary lithium-ion batteries include commercially available cells, such as those available from A123 Systems located in Watertown, Mass. In one embodiment, the cells have a nominal amp-hour rating of 2.3 Ah and a nominal load voltage of 3.3 DCV/cell. Further exemplary lithium-ion batteries include commercially available cells available from SAFT America, Inc. located at 313 Crescent St Ne in Valdese, N.C. in Watertown, Mass. In one embodiment, the cells have a nominal maximum current of 500 A, a specific power of 5.1 kW/kg, a specific energy of 430 kJ/kg, and a mass of 0.94 kg.

Figure 19:
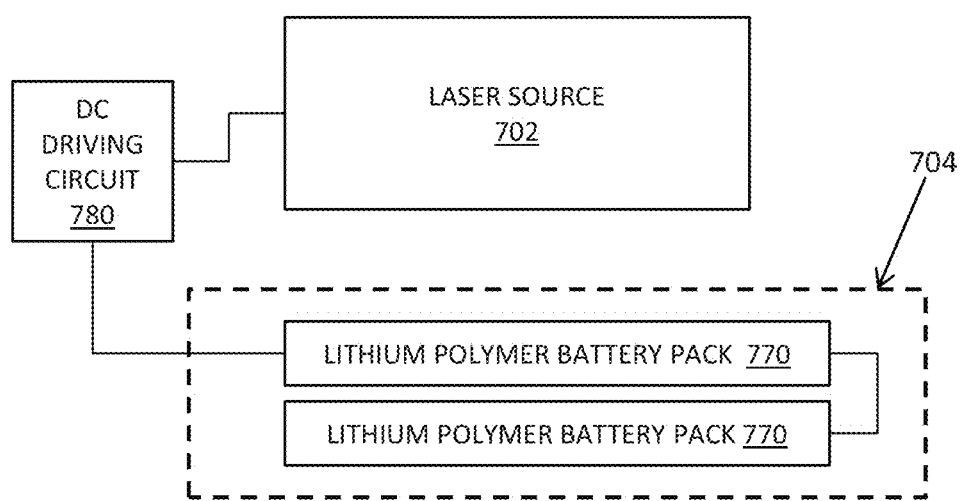
FIG. 19 is a representative view of an exemplary portable battery power supply.

Referring to FIG. 19, multiple lithium-ion battery packs 770 are coupled together in series to produce power supply 704. Each of lithium-ion battery pack 770 delivers about 5 kilowatts of power for about six minutes. Since two units are shown coupled together in FIG. 19, the resultant power supply 704 can deliver about 10 kilowatts of power. Each of lithium-ion battery pack 770 includes multiple individual lithium-ion batteries. In one embodiment, lithium-ion battery pack 770 commercially available cells available from A123 Systems located in Watertown, Mass. The two lithium-ion battery packs 770 together weigh about 28 pounds (13.6 kg).

Figure 20:
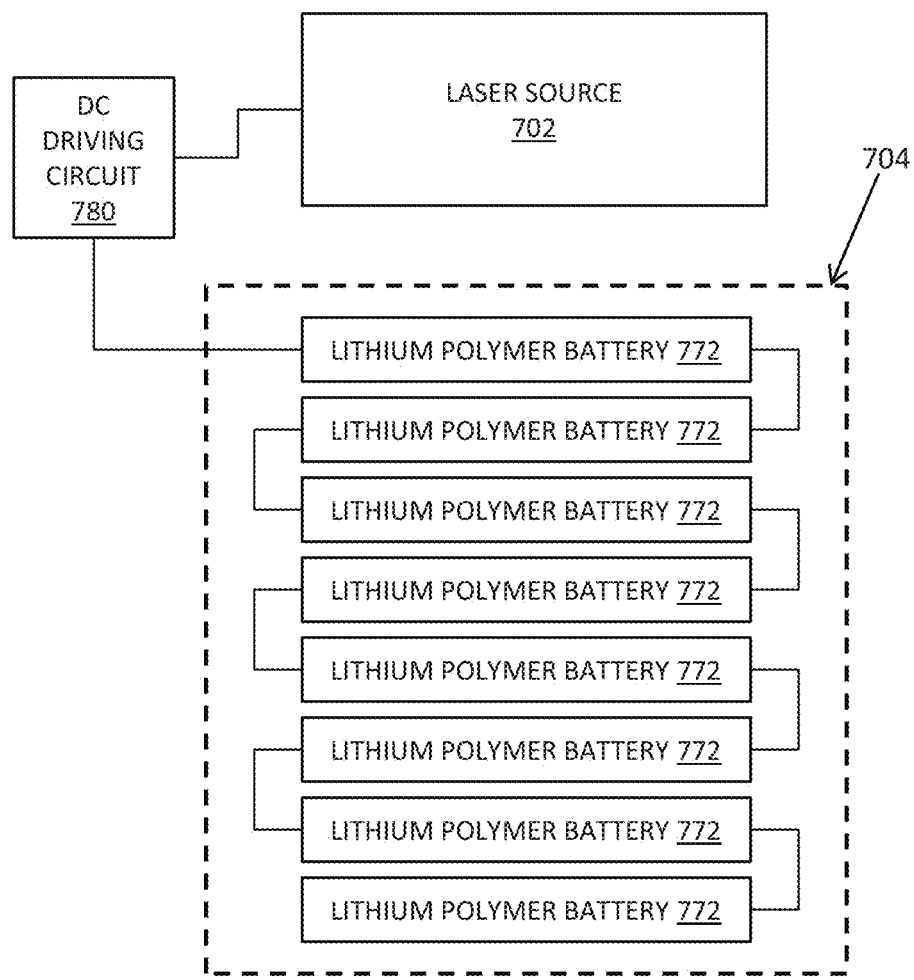
FIG. 20 is a representative view of an exemplary second portable battery power supply.

Referring to FIG. 20, multiple lithium polymer batteries 772 are coupled together in series to produce power supply 704. Each of lithium polymer batteries 772 delivers about 4.5 kilowatts of power for about two minutes. Since eight units are shown coupled together in FIG. 20, the resultant power supply 704 can deliver about 13 kilowatts of power for about six minutes. The eight lithium polymer batteries 772 together weigh about 21 pounds (9.6 kg).

In one embodiment, laser source 702 is a three kilowatt Yterrbium single mode fiber laser such as ones commercially available from IPG Photonics located at IPG Photonics Corporation, 50 Old Webster Road Oxford, Mass. 01540 USA and power supply 704 is as shown in FIG. 20. This combination results in portable cutting device 700 having a cutting speed of about fifty inches per minute for 0.5 inch thick steel. This combination may cut up to 900 inches of material on a single charge of power supply 704, arranged as shown in FIG. 20. In general, commercial laser sources include an AC-to-DC converter to convert power from an AC source to DC power for laser source 702. Since power supply 704 already provides DC power, when a commercial laser source is being used the AC-to-DC converter is removed and replaced with DC driving circuit 780. DC driving circuit 780 provides power from power supply 704 to laser source 702 and regulates the power level provided. In a similar fashion, commercial laser sources often include cooling lines to cool the laser source and over-temperature sensors to monitor the temperature of the laser source. In one embodiment, when a commercial laser source is being used the cooling lines are removed and the over-temperature sensors of the commercial laser source are overridden. With this arrangement and using the laser directing device 708 represented in FIG. 21, laser directing device 708 was operated at 3 kW power for 720 seconds without disabling the laser source 702.

Figure 25:
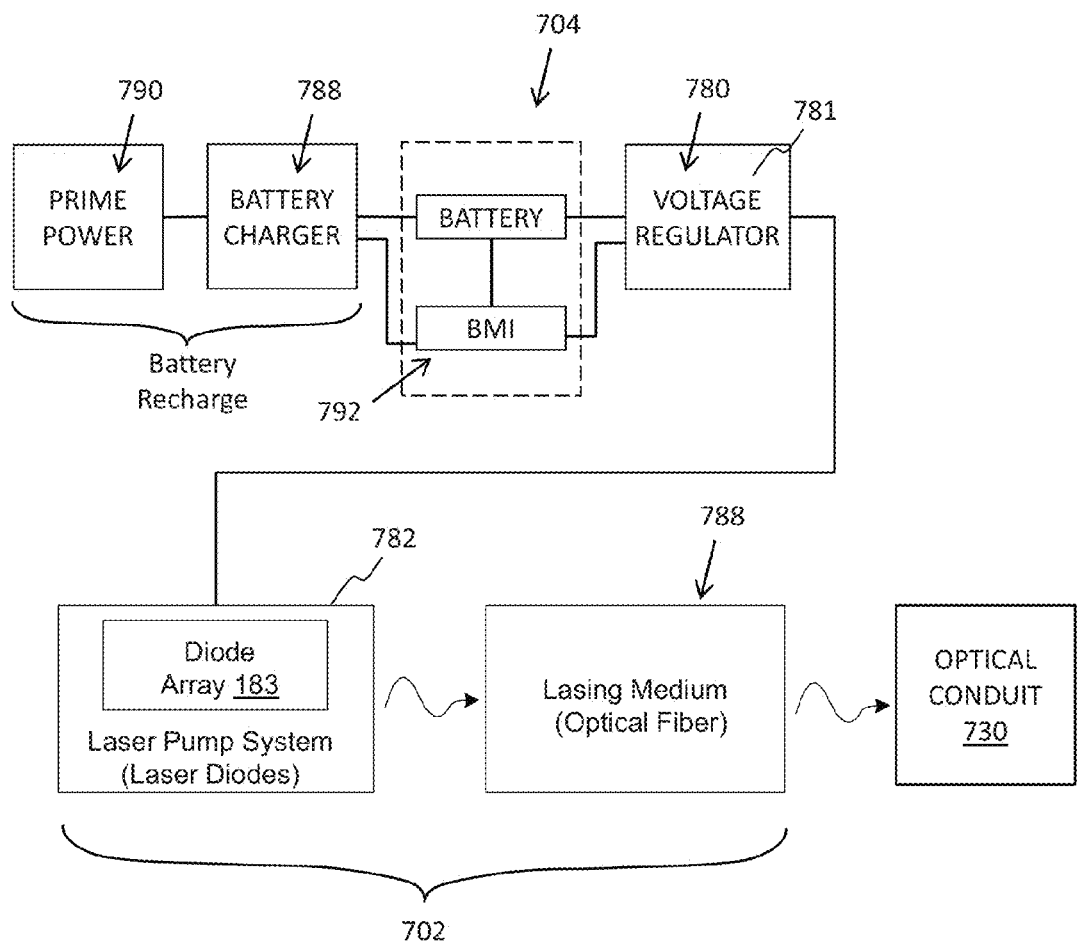
FIG. 25 illustrates a first arrangement of components of the portable cutting device.
Figure 26:
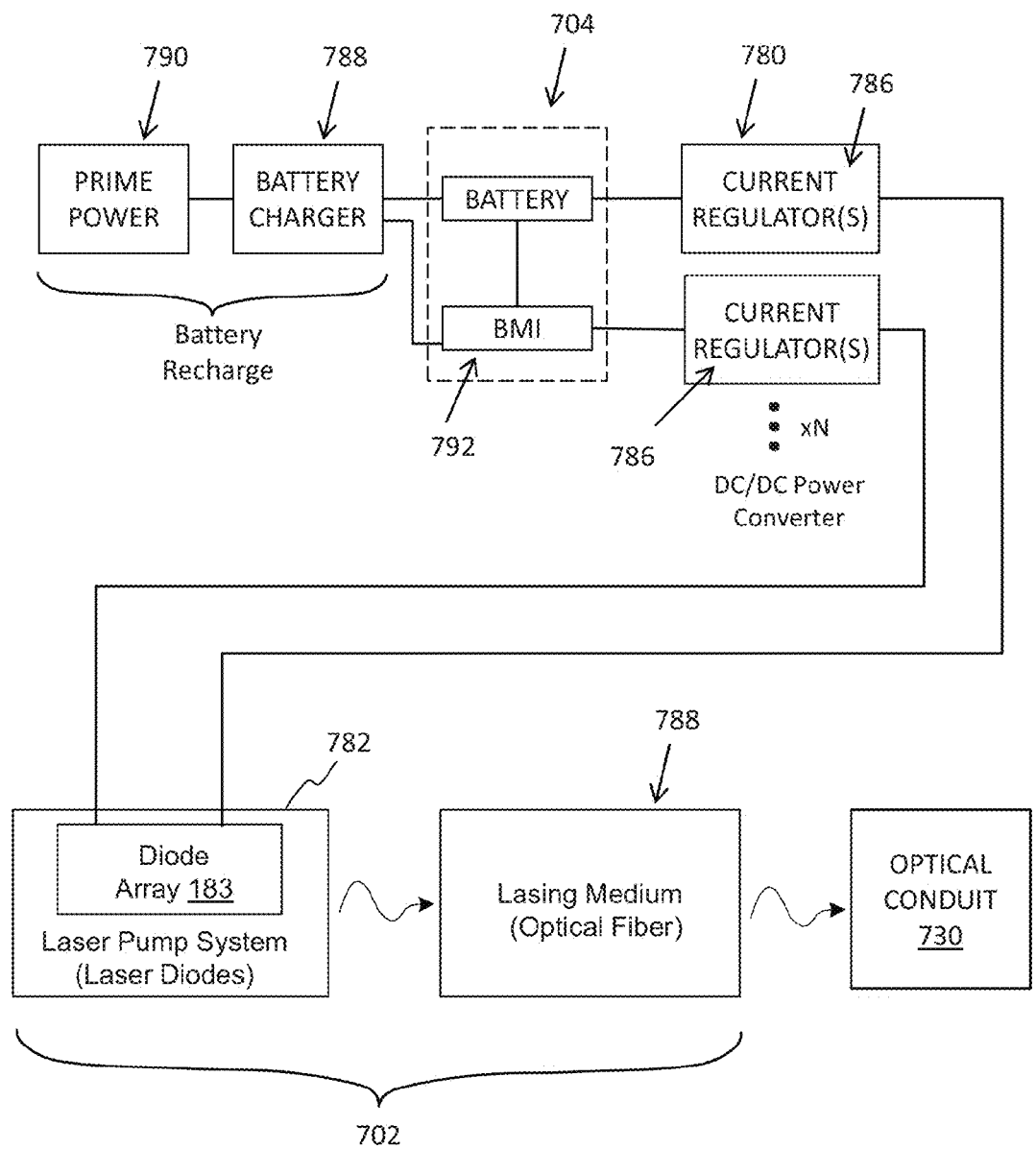
FIG. 26 illustrates a second arrangement of components of the portable cutting device.

Referring to either FIG. 25 or FIG. 26, laser source 702 is represented. Laser source 702 includes a laser pump system 782 which includes a plurality of laser diodes 783. Laser diodes 783 provide the pump energy for the lasing medium 784 of laser source 702. The laser diodes 783 are divided into a plurality of modules. In one embodiment, 42 diodes are provided in a single module and seven modules are provided. The lasing medium 784 is provided as part of a fiber optical cable. The output of the lasing medium 784 is provided to optical conduit 730.

In FIG. 25, power supply 704 is coupled to laser diodes 783 through DC driving circuit 780 which includes a single voltage regulator 781 that powers laser diodes 783. In FIG. 26, power supply 704 is coupled to laser diodes 783 through DC driving circuit 780 which includes a plurality of current regulators 786. Each current regulator 786 provides the power to one of the modules to provide power to the diodes of that module.

Referring to either FIG. 25 or FIG. 26, power supply 704 may be charged with a battery charger 788 coupled to prime power source 790. Exemplary prime power sources include a standard AC wall outlet or an alternator of a vehicle. Power supply 704 includes a battery management interface 792 which controls the recharging of the batteries with battery charger 788.

Figure 21:
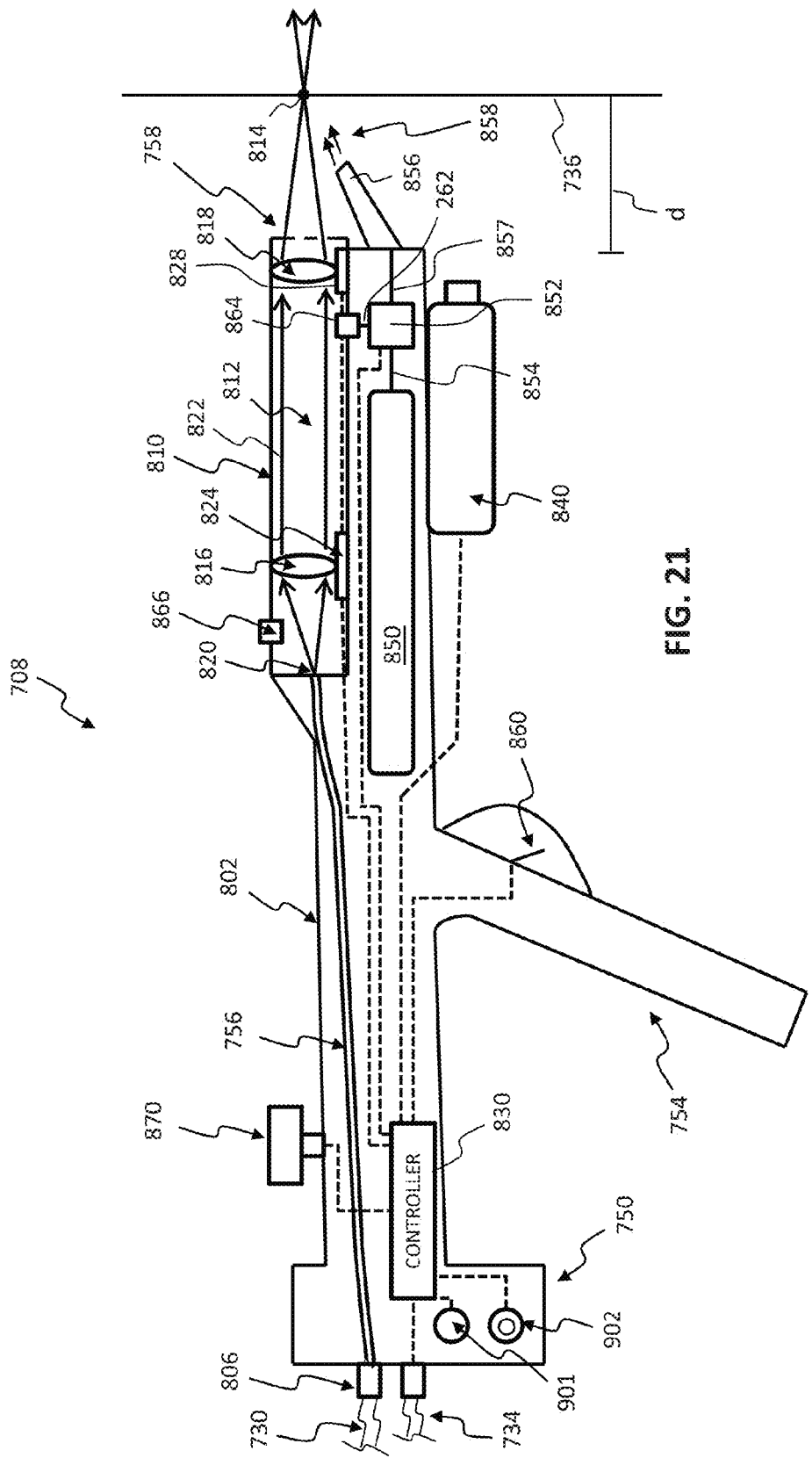
FIG. 21 is a representative view of a laser directing device of the portable cutting device of FIG. 18.

Referring to FIG. 21, an exemplary embodiment of laser directing device 708 is shown. Laser directing device 708 has a body 802 with a downwardly extending handle 804. Optical conduit 730 is coupled to an optical connector 806 which couples optical conduit 730 to optical conduit 808. Optical conduit 808 is coupled to a collimating chamber 810.

Collimating chamber 810 includes an optical system 812 which focuses light carried by optical conduit 808 at a focus 814 generally corresponding to the location of barrier 736. In one embodiment, the focal range of laser directing device 708 is from about six inches from end 758 to about sixty feet from end 758. In one embodiment, the focal range of laser directing device 708 is from about six inches from end 758 to about three kilometers from end 758.

In the illustrated embodiment, optical system 812 includes a first lens 816 and a second lens 818. First lens 816 receives the light from optical conduit 808 which acts like a point source. In the illustrated embodiment, first lens 816 is positioned such that an end 820 of optical conduit 808 is located at a focus of first lens 816 which results in a generally collimated beam 822 being produced inside of collimating chamber 810. Second lens 818 focuses collimated beam 822 at barrier 736. Although a two lens system is shown, other lens systems may be used to focus the light at focus 814.

The position of one or both of first lens 816 and second lens 818 may be altered relative to the position of end 820 of optical conduit 808 or the other of first lens 816 and second lens 818 to change the location of focus 814. In one embodiment, a portion of collimating chamber 810 is moveable relative to the remainder of collimating chamber 810 to allow an operator to manually adjust the relative spacing of first lens 816 and second lens 818 similar to a scope on a rifle. In one embodiment, first lens 816 is positioned on a moveable stand 824 and second lens 818 is positioned on a moveable stand 826. Both of moveable stand 824 and moveable stand 826 are controlled through respective motors to adjust the position of the respective first lens 816 and second lens 818.

The motors are controlled by a controller 830 of laser directing device 708. In one embodiment, controller 830 receives an input from an operator control (not shown) through which the operator specifies the desired position of focus 814. In one embodiment, controller 830 receives an input from a laser rangefinder 840 which determines the distance d from laser directing device 708 to barrier 736. Based on the determined distance d, controller 830 moves one or both of first lens 816 and second lens 818 to place focus 814 at distance d. In one embodiment, other locating devices may be used, such as GPS systems.

In one embodiment, instead of or in addition to a laser range finder device 840 includes a visible guide laser which provides a visible marker for the operator of where laser directing device 708 is going to cut. The visible guide laser should be collinear with an axis of collimating chamber 810. In one example, the visible guide laser is a HeNe laser. In one embodiment, laser source 702 acts as a guide laser. The operator wears goggles which can detect and provide a visible image of the barrier and the laser source at the barrier. In this embodiment, the laser source can be set to a low power setting to align with barrier and then set to a high power setting to cut barrier.

Laser directing device 708 also includes a compressed gas container 850 which provides air to a regulator valve 852 through a conduit 854. Regulator valve 852 provides gas to a nozzle 856 through a conduit 857. Nozzle 856 directs gas 858 at focus 814. In one embodiment, the position of nozzle 856 is adjustable. The gas blows molten material produced during cutting away from laser directing device 708, the operator, and away from barrier 736. Controller 830 controls regulator valve 852 to place conduit 857 in fluid communication with conduit 854 when a trigger 860 of laser directing device 708 is pulled by the operator. In one embodiment, the gas stored in compressed gas container 850 is a non-flammable gas. Exemplary gases include freon, nitrogen, argon, and other non-flammable gases.

Controller 830 also controls regulator valve 852 to place conduit 854 in fluid communication with a fluid conduit 862. Fluid conduit 862 terminates at a fluid inlet 864 to collimating chamber 810. The gas presented to collimating chamber 810 cools first lens 816 and second lens 818 from the heat generated by the light from optical conduit 808. Warmer gas in collimating chamber 810 is exhausted through a fluid outlet 866 of collimating chamber 810. In one embodiment, controller 830 controls regulator valve 852 to provide gas to fluid conduit 862 whenever trigger 860 is pulled. In one embodiment, controller 830 controls regulator valve 852 to provide gas to fluid conduit 862 when a temperature sensor monitoring collimating chamber 810 detects an elevated temperature.

Figure 22A:
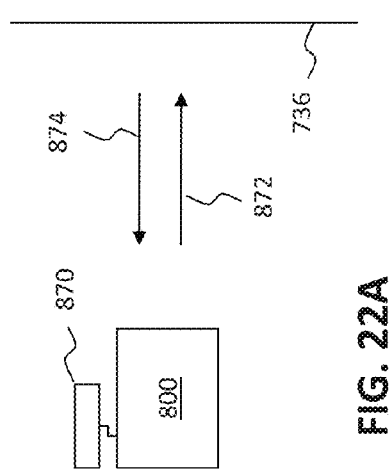
FIG. 22A illustrates a first positioning of the laser directing device relative to the barrier.

Laser directing device 708 further includes a sensor 870 which monitors for light having generally the same wavelength provided by laser directing device 708 at focus 814. Sensor 870 monitors the intensity of the light reflected from barrier 736. Referring to FIG. 22A, when laser directing device 708 is generally normal to barrier 736, the light (represented by arrow 872) focused by laser directing device 708 strikes barrier 736 generally normal to barrier 736. A portion of the light (represented by arrow 874) is reflected by barrier 736. Often the reflected portion is small compared to the portion which interacts with barrier 736 to cut barrier 736 and as such does not pose a threat to the operator. However, when barrier 736 is more reflective the strength of the reflected portion increases. When a 1.07 micrometer wavelength beam is used, irradiance levels of about 5 milli-watts per square centimeter ($mW/cm^2$) pose a threat to the operator at any range less than 77 km, such as damage to the retina of the eye. At wavelengths less than 1.55 micrometer, light is transmitted into the eye which can damage the retina. In one embodiment, a laser source 702 having a wavelength of at least 1.55 micrometer is used. In one embodiment, a laser source 702 having a wavelength of about 2.0 micrometer is used. At wavelengths of 1.55 micrometer and greater, damage to the cornea of the eye is the concern. Since the cornea heals quite easily and the retina is generally permanently damaged, wavelengths which are absorbed by the cornea and not transmitted are considered to be "eye safe".

By monitoring the irradiance levels of the reflected portion with sensor 870, controller 830 may make a determination of actions to take. In one embodiment, if the irradiance levels of the reflected portion are above a first threshold, controller 830 sends an instruction to controller 705 to shut down laser source 702. In one embodiment, the first threshold is about 2.5 $mW/cm^2$.

Figure 22B:
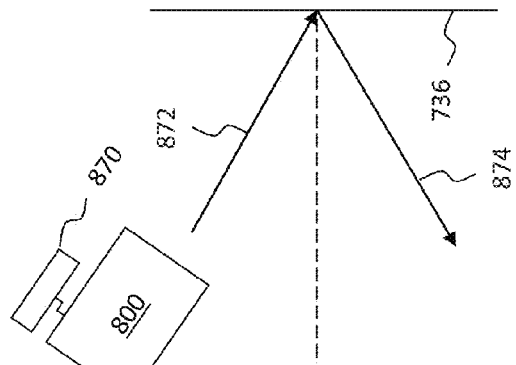
FIG. 22B illustrates a second positioning of the laser directing device relative to the barrier.

In one embodiment, if the irradiance levels of the reflected portion are above a first threshold, controller 830 sounds an alarm which provides an indication to the operator that the irradiance levels of the reflected portion are elevated, but not at a threatening level. The operator may then move to the arrangement shown in FIG. 22B, wherein the light represented by arrow 872 is not normal to barrier 736; thereby causing the reflected light represented by arrow 874 to not be returned to sensor 870. However, if the irradiance levels are above a second threshold, controller 830 sends an instruction to controller 705 to shut laser source 702 down. In one embodiment, the first threshold is about 2.0 $mW/cm^2$ and second threshold is about 2.5 $mW/cm^2$.

Figure 23:
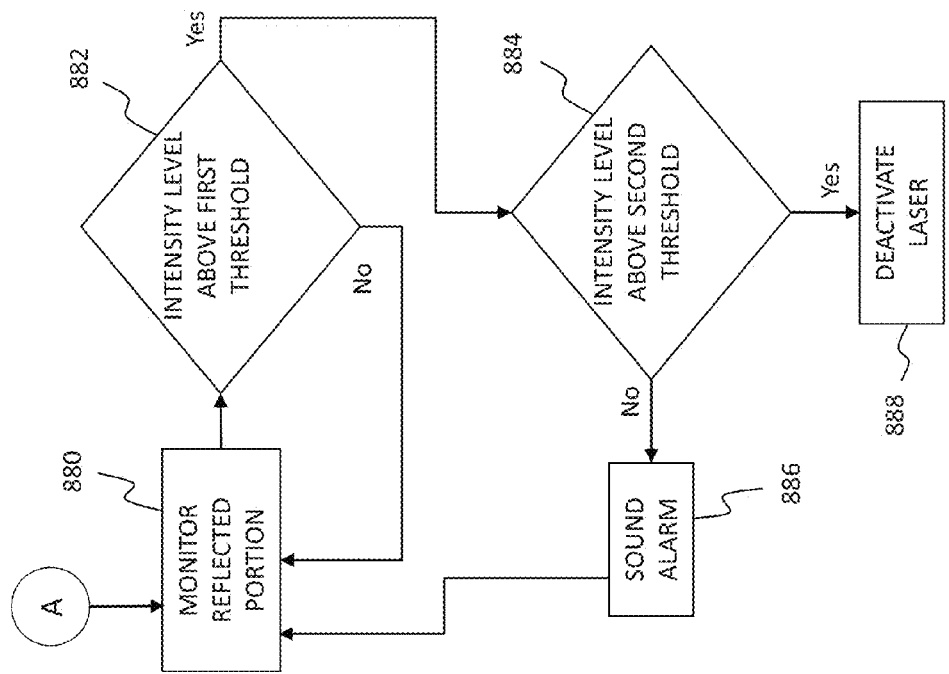
FIG. 23 illustrates a processing sequence of a controller of the portable cutting device.

This control sequence is represented in FIG. 23. The irradiance level of the reflected portion is monitored with sensor 870, as represented by block 880. The irradiance level is compared to a first threshold, as represented by block 882. If the irradiance level is below the first threshold, no action is taken and the irradiance level of the reflected portion is continued to be monitored with sensor 870. If the irradiance level is at or above the first threshold, then the irradiance level is compared to a second threshold, as represented by block 884. If the irradiance level is not at or above the second threshold, then an alarm is sounded, as represented by block 886. This informs the operator that irradiance levels are elevated and that action should be taken, such as changing the angle of incidence relative to barrier 736. Exemplary alarms include audio alarms (such as speakers), visual alarms (such as lights), tactile alarms (such as vibrating members), or combinations thereof. If the irradiance level is at or above the second threshold, then laser source 702 is deactivated, as represented by block 888.

Returning to FIG. 21, laser directing device 708 further includes a safety switch 901 and a laser power setting switch 902. Safety switch 901 provides a safety in case the operator inadvertently pulls trigger 860. Safety switch 901 may be a toggle switch, a dial, or any other suitable input device. Laser power setting switch 902 provides an indication of the desired power level of laser source 702. By running laser source 702 at lower power levels for applications not requiring high power settings, the charge life of power supply 704 may be extended. Laser power setting switch 902 may be any type of input devices which provides multiple settings, each corresponding to a particular power level. An exemplary input device is a dial. In one embodiment, the power level of laser source 702 may be adjusted from 0% to 100%.

Figure 24:
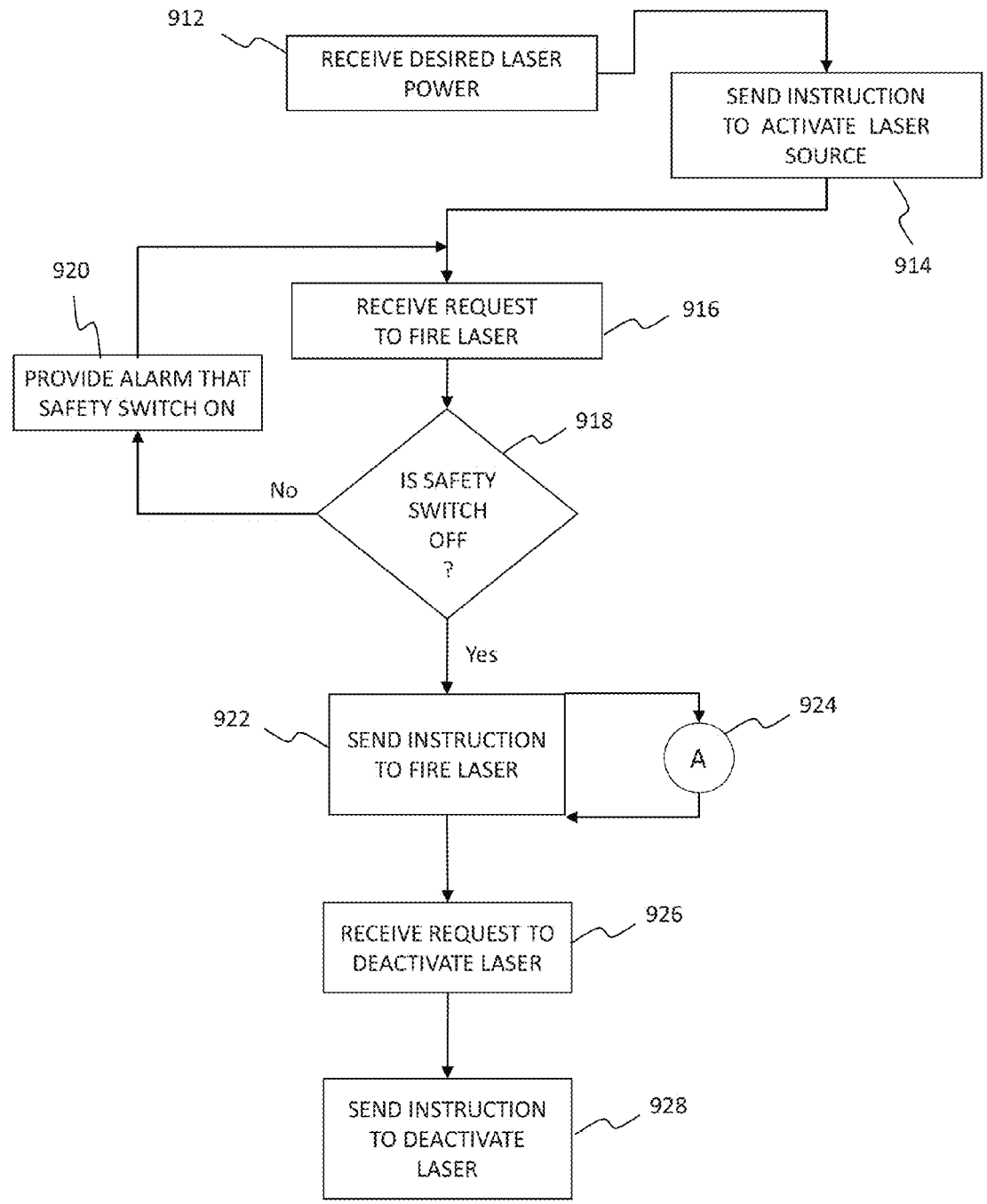
FIG. 24 illustrates another processing sequence of the controller of the portable cutting device.

Referring to FIG. 24, an exemplary operation sequence for laser directing device 708 is provided. A request is received by controller 830 to set the desired power level of laser source 702, as represented by block 912. For laser directing device 708, the request to set the desired power level of laser source 702 is the setting of laser power setting switch 902. Controller 830 sends an instruction to controller 705 to activate laser source 702 at the desired power level, as represented by block 914.

Controller 830 receives a request to fire laser source 702, as represented by block 916. For laser directing device 708, the request to fire laser source 702 is the pulling of trigger 860 which is monitored by controller 830. Controller 830 checks to see if the safety switch 901 is off, as represented by block 918. For laser directing device 708, the state of safety switch 901 is checked. If the safety switch is on, an alarm is provided to alert the operator that the safety is on, as represented by block 920. Exemplary alarms include audio alarms (such as speakers), visual alarms (such as lights), tactile alarms (such as vibrating members), or combinations thereof. If the safety switch is off, then controller 830 sends an instruction to controller 705 to fire laser source 702, as represented by block 922.

While laser source 702 is being fired, the monitoring sequence of FIG. 23 is carried out, as represented by block 924. Controller 830 receives a request to deactivate laser source 702, as represented by block 926. For laser directing device 708, the request to deactivate laser source 702 is the release of trigger 860 which is monitored by controller 830. Controller 830 sends an instruction to controller 705 to deactivate laser source 702, as represented by block 928.

With trigger 860 pulled, operator 720 moves laser directing device 708 with his/her arms to define the cutting path of laser directing device 708. As such, laser directing device 708 may be moved by human operator 720 without the need to also move laser source 702. This flexibility is provided in part by the flexibility of optical conduit 730. As represented in FIG. 18, a planned cutting path 762 is shown including a first portion 764 which has already been cut. Once cutting is complete, portable cutting device 700 may be powered off, by letting trigger 860 released. In between cutting operations, power supply 704 may be recharged or replaced.

Figure 29:
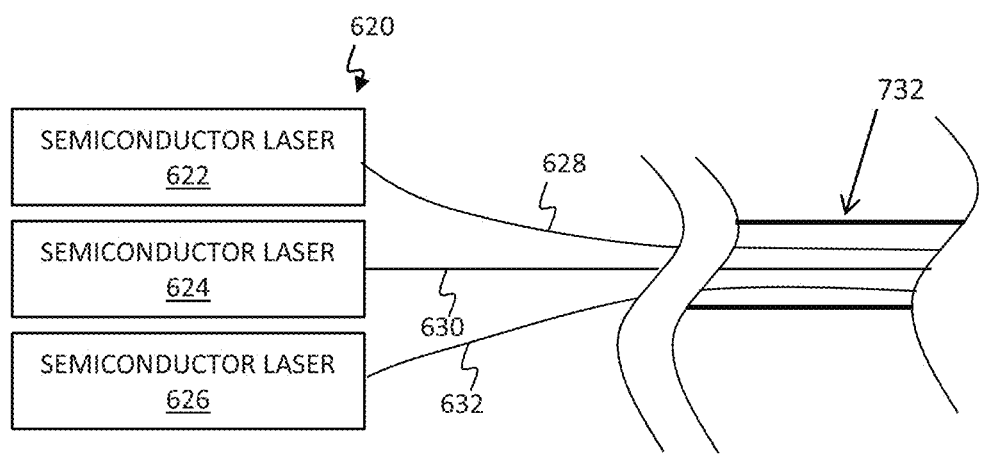
FIG. 29 a representative view of a portion of a portable cutting device.

Referring to FIG. 29, in one embodiment, the laser source 702 of portable cutting device 700 includes a laser source 620. Laser source 620 includes a plurality of semiconductor lasers 622-626 which produce optical energy for portable cutting device 700. In one embodiment, the semiconductor lasers are continuous wave lasers. In one embodiment, lasers 622-626 are quantum cascade lasers. Exemplary quantum cascade lasers include External Cavity Quantum Cascade Lasers available from Daylight Solutions located at 13029 Danielson Street, Suite 130 in Poway, Calif. and Pranalytica located at 1101 Colorado Avenue in Santa Monica, Calif. In one embodiment, the semiconductor lasers have a wavelength of at least about 1 um. In one embodiment, the semiconductor lasers have a wavelength of at least about 2 um.

The output optical energy of each of lasers 622-626 is carried through respective optical conduits 628-632. In one embodiment, the output of each of optical conduits 628-632 is combined and passes through optical conduit 730 to laser directing device 708. In the illustrated embodiment, each of optical conduits 628-632 pass through optical conduit 730. In this example, the end of each of optical conduits 628-632 generally coincide with optical connector 806. optical conduit 756 then propagates the optical energy to optical system 812 which outputs the optical energy from laser directing device 708. The optical energy of lasers 602-606 is generally incoherently combined to produce a beam with a power level sufficient to function in the same manner as laser source 702. In one embodiment, the power of the combined lasers 602-606 is about 3 kilowatts. In one embodiment, the power level of combined lasers 602-606 is about 5 kilowatts. In one embodiment, the power level of combined lasers 602-606 is about 10 kilowatts. In one embodiment, the power level of combined lasers 602-606 is about 20 kilowatts. In one embodiment, the power level of combined lasers 602-606 is about 50 kilowatts. In one embodiment, the power level of combined lasers 602-606 is between about 3 kilowatts and 20 kilowatts. In one embodiment, the power level of combined lasers 602-606 is at least 3 kilowatts.

In one embodiment, portable cutting device 700 is mounted to a moveable platform so that portable cutting device 700 is positionable relative to various objects to be cut or removed without having to be held by an operator. The portable cutting device may be fired at an object having a first hardness. Subsequent to firing, the hardness of the object is reduced it is believed due to the interaction of the optical energy produced by portable cutting device 700 and the object. Once the hardness of the object has been reduced a mechanical tool may be used to remove at least portions of the object. In one example, the portable cutting device 700 is lowered into a well shaft and fired at rock in the well shaft to reduce the hardness of the rock. Subsequent thereto, a mechanical drill is used to further breakup and remove the rock from the well shaft.

Although the disclosed systems have included laser systems with wavelengths in the infrared spectrum, the teaching presented herein may also be used with laser systems with wavelengths in the visible spectrum or ultraviolet spectrum.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. An apparatus for interacting with a mobile tracking device, the apparatus comprising:
a body;
at least one propulsion device supported by the body;
a plurality of sensor modules supported by the body which monitor the environment surrounding the body;
a controller operatively connected to the plurality of sensor modules, the controller determining a presence of the mobile tracking device in the environment surrounding the body based on information collected by the plurality of sensor modules and a current location of the mobile tracking device comprising a type of mobile tracking device which is identified based on a retro-reflection received from mobile tracking device;
a modulation system which receives the current location of the mobile tracking device from the controller, orients a tracking system of the modulation system based on the current location of the mobile tracking device, detects the mobile tracking device, updates the location of the mobile tracking device, and directs a continuous beam of optical energy at the mobile tracking device, the continuous beam of optical energy being produced by a plurality of semiconductor lasers whose output are combined, wherein said beam is directed towards and is received by a telescope within said mobile tracking device, wherein said beam is configured to produce different effects on said mobile tracking device receiving said optical energy based on a separation distance of said mobile tracking device from the modulation device, wherein said separation comprises distance that is divided into three ranges comprising a near distance band, a mid-distance band, and a far distance band, wherein at distances in near distance band energy of said beam explodes seeker head and destroys mobile tracking device, at distances in mid distance band the beam destroys functionality of detector, wherein distances in said far distance band the beam produces a plurality of internal localized infrared radiation sources within said mobile tracking device, said internal localized sources are produced by the beam being absorbed by optical components of mobile tracking device which then reradiate absorbed energy in multiple wavelengths within the mobile tracking device, wherein the beam produces infrared energy which is brighter than infrared signature of an asset initially being tracked by said mobile tracking device such that a controller of said mobile tracking device interprets reradiated absorbed energy within the mobile tracking device as the infrared signature of the asset, wherein if internal reradiated energy is off-axis of the infrared signature of said asset, controller will generate an erroneous guidance signal that causes said mobile tracking device to alter the mobile tracking device's path of travel away from said asset.

2. The apparatus of claim 1, wherein the plurality of semiconductor lasers are quantum cascade lasers.

3. The apparatus of claim 1, wherein the output of each of the plurality of semiconductor lasers are incoherently combined to produce the continuous beam of optical energy.

4. The apparatus of claim 1, wherein the controller continues to update the current location of the mobile tracking device until the modulation system detects the mobile tracking device, the modulation system using the updated current location to orient the tracking system.

5. The apparatus of claim 4, wherein the plurality of sensor modules have a wide field of view to survey the environment around the body and the modulation system has a narrower field of view to focus on the location of the mobile tracking device.

6. The apparatus of claim 1, wherein the modulation system includes a beam control module which controls a direction of the continuous beam of optical energy based on the updated location of the mobile tracking device.

7. The apparatus of claim 6, wherein the continuous beam of optical energy is provided until the beam control module has caused the direction of the continuous beam of optical energy to move by a predetermined threshold amount.

8. The apparatus of claim 7, wherein the predetermined threshold amount is three degrees.

9. The apparatus of claim 2, wherein the modulation system includes a beam control module which controls a direction of the continuous beam of optical energy based on the updated location of the mobile tracking device, the beam control module being coupled to said semiconductor lasers comprising a continuous wave fiber laser through an optical conduit.

10. The apparatus of claim 9, wherein the modulation system includes a housing and beam control module includes a positioning system which includes a rotatable head coupled to the housing and including an optical window through which the continuous beam of optical energy exits counter measure system, the positioning system rotating the rotatable head to control the direction of the continuous beam of optical energy.

11. The apparatus of claim 10, wherein the positioning system further includes a moveable optical component which may be moved to control the direction of the continuous beam of optical energy.

12. An apparatus for use with an asset and for interacting with a mobile tracking device, the apparatus comprising:
   a pod configured to be attached to the asset, the pod including an optical window;
   a plurality of continuous wave semiconductor lasers positioned within the pod;
   a controller positioned within the pod operatively connected to the plurality of sensor modules, the controller determining a presence of the mobile tracking device in the environment surrounding the body based on information collected by the plurality of sensor modules and a current location of the mobile tracking device;
   a modulation and beam directing system positioned within the pod which receives the current location of the mobile tracking device from the controller, orients a tracking system of the modulation system based on the current location of the mobile tracking device, detects the mobile tracking device, updates the location of the mobile tracking device, and directs a continuous beam of optical energy produced from said continuous wave lasers at the mobile tracking device, the continuous beam of optical energy being produced by a plurality of semiconductor lasers whose output are combined; and
   a battery source operatively coupled to the plurality of continuous wave semiconductor lasers and positioned within the pod, the battery source providing power to the plurality of continuous wave semiconductor lasers to produce a continuous beam of optical energy;
   wherein said beam is directed towards and is received by a telescope within said mobile tracking device, wherein said beam is configured to produce different effects on said mobile tracking device receiving said optical energy based on a separation distance of said mobile tracking device from the modulation device, wherein said separation comprises distance that is divided into three ranges comprising a near distance band, a mid-distance band, and a far distance band, wherein at distances in near distance band energy of said beam explodes seeker head and destroys mobile tracking device, at distances in mid distance band the beam destroys functionality of detector, wherein distances in said far distance band the beam produces a plurality of internal localized infrared radiation sources within said mobile tracking device, said internal localized sources are produced by the beam being absorbed by optical components of mobile tracking device which then reradiate absorbed energy in multiple wavelengths within the mobile tracking device, wherein the beam produces infrared energy which is brighter than infrared signature of an asset initially being tracked by said mobile tracking device such that a controller of said mobile tracking device interprets reradiated absorbed energy within the mobile tracking device as the infrared signature of the asset, wherein if internal reradiated energy is off-axis of the infrared signature of said asset, controller will generate an erroneous guidance signal that causes said mobile tracking device to alter the mobile tracking device's path of travel away from said asset.

13. The apparatus of claim 12, wherein the pod includes a rotatable head having an optical window through which the continuous beam of optical energy exits the pod.

14. The apparatus of claim 12, further comprising a battery charger positioned within the pod and coupled to a power source of the asset, the battery charger charging the battery source when the asset is operating in a low power mode.

15. The apparatus of claim 12, further comprising a laser designator positioned within the pod, the laser designator determining a distance from the pod to the mobile tracking device.

16. The apparatus of claim 15, wherein the continuous beam of optical energy is focused at a distance shorter than the distance from the pod to the mobile tracking device determined by the laser designator.

17. A method for keeping a mobile tracking device away from an asset, the mobile tracking device having a seeker head which is directed at an asset due to the infrared energy radiated by the asset, the method comprising the steps of:
   identifying a presence of a mobile tracking device based on at least one sensor and determining a type of mobile tracking device which is identified based on a retro-reflection received from a seeker head in the mobile tracking device;
   directing a combined output of a plurality of continuous wave semiconductor lasers comprising a beam at the seeker head along a first direction of travel of the mobile tracking device, the combined output of a plurality of continuous wave semiconductor lasers being infrared energy, wherein said beam is directed towards and is received by a telescope within said mobile tracking device, wherein said beam is configured to produce different effects on said mobile tracking device receiving said optical energy based on a separation distance of said mobile tracking device from the modulation device, wherein said separation comprises distance that is divided into three ranges comprising a near distance band, a mid-distance band, and a far distance band; and
   propagating the infrared energy from the plurality of continuous wave semiconductor lasers into the seeker head of the mobile tracking device to generate said different effects, wherein at distances in near distance band energy of said beam explodes seeker head and destroys mobile tracking device, at distances in mid distance band the beam destroys functionality of detector, wherein distances in said far distance band the beam produces at least one localized source within the mobile tracking device and within a field of view of the mobile tracking device which indicates a second direction of travel for the mobile tracking device, said internal localized sources are produced by the beam being absorbed by optical components of mobile tracking device which then reradiate absorbed energy in multiple wavelengths within the mobile tracking device, wherein the beam produces infrared energy which is brighter than infrared signature of an asset initially being tracked by said mobile tracking device such that a controller of said mobile tracking device interprets reradiated absorbed energy within the mobile tracking device as the infrared signature of the asset, wherein if internal reradiated energy is off-axis of the infrared signature of said asset, controller will generate an erroneous guidance signal that causes said mobile tracking device to alter the mobile tracking device's path of travel away from said asset.

18. The method of claim 17, further comprising the steps of:

altering the direction of the combined output of the plurality of continuous wave semiconductor lasers such that the combined output of the plurality of continuous wave semiconductor lasers continues to be directed at the seeker head of the mobile tracking device which is traveling in the second direction.

19. The method of claim 17, wherein the plurality of continuous wave semiconductor lasers are quantum cascade lasers.

20. A method for keeping a mobile tracking device away from an asset, the mobile tracking device having a seeker head which is directed at an asset due to the infrared energy radiated by the asset, the method comprising the steps of:

identifying a presence of a mobile tracking device based on at least one sensor and determining a type of mobile tracking device which is identified based on a retro-reflection received from a seeker head in the mobile tracking device;

activating a plurality of continuous wave semiconductor lasers;

directing a combined beam of infrared energy from the plurality of continuous wave semiconductor lasers at the mobile tracking device, wherein the combined beam of infrared energy causes the mobile tracking device to explode in a first separation band; causes components of the mobile tracking device to become inoperative in a second separation band, the second separation band corresponding to distances longer than first separation band; and causes localized internal sources within the seeker head which cause the mobile tracking device to alter its direction of travel away from the asset in a third separation band, the third separation band corresponding to distances longer than the second separation band.

* * * * *